US010649545B2

(12) United States Patent
Madsen

(10) Patent No.: US 10,649,545 B2
(45) Date of Patent: May 12, 2020

(54) ADAPTIVE, MULTIMODAL COMMUNICATION SYSTEM FOR NON-SPEAKING ICU PATIENTS

(71) Applicant: University of Massachusetts, Boston, MA (US)

(72) Inventor: Miriam Madsen, Worcester, MA (US)

(73) Assignee: University of Massachusetts, Boston, MA (US)

( * ) Notice: Subject to any disclaimer, the term of this patent is extended or adjusted under 35 U.S.C. 154(b) by 70 days.

(21) Appl. No.: 15/778,971

(22) PCT Filed: Dec. 12, 2016

(86) PCT No.: PCT/US2016/066081
§ 371 (c)(1),
(2) Date: May 24, 2018

(87) PCT Pub. No.: WO2017/100737
PCT Pub. Date: Jun. 15, 2017

(65) Prior Publication Data
US 2018/0348894 A1    Dec. 6, 2018

Related U.S. Application Data

(60) Provisional application No. 62/266,558, filed on Dec. 11, 2015.

(51) Int. Cl.
| G06F 3/033 | (2013.01) |
| G06F 3/0338 | (2013.01) |
| G09B 21/00 | (2006.01) |
| G16H 40/63 | (2018.01) |
| G16H 40/20 | (2018.01) |
| G06F 19/00 | (2018.01) |

(Continued)

(52) U.S. Cl.
CPC ............ *G06F 3/0338* (2013.01); *G06F 19/00* (2013.01); *G09B 21/00* (2013.01); *G09B 21/009* (2013.01); *G16H 40/20* (2018.01); *G16H 40/63* (2018.01); *G16H 80/00* (2018.01); *G06F 3/02* (2013.01)

(58) Field of Classification Search
CPC .......... G06F 3/0338; G06F 3/02; G06F 19/00; G09B 21/00; G09B 21/009; G16H 80/00; G16H 40/20; G16H 40/63
See application file for complete search history.

(56) References Cited

U.S. PATENT DOCUMENTS

| 2008/0312902 A1* | 12/2008 | Dollinger | G06F 17/289 704/4 |
| 2012/0278104 A1* | 11/2012 | Traughber | G08B 5/222 705/3 |
| 2014/0340372 A1* | 11/2014 | Olsson | G06F 3/0338 345/184 |

* cited by examiner

*Primary Examiner* — Liliana Cerullo
(74) *Attorney, Agent, or Firm* — Milstein Zhang & Wu LLC

(57) ABSTRACT

A communication system for use by individuals whose ability to speak is restricted, such as intubated patients in a hospital setting. Apparatus is provided to allow such a person to input his or her responses to topics of interest and thereby to communicate with others, such as medical professionals. In some embodiments the input is a joystick-like device that allows selections to be made in response to displayed option on a screen. In some embodiments, a digitally operated setoff keys is provided. The user's inputs are processed in a general purpose programmable computer that operates under the control of a set of non-volatile instructions recoded on a machine-readable medium.

10 Claims, 26 Drawing Sheets

(51) Int. Cl.
*G16H 80/00* (2018.01)
*G06F 3/02* (2006.01)

Your name is John Smith.

You are currently at UMass Hospital in the Surgical ICU.

It is 8:11 AM on Tuesday, 12/1/2015.

FIG. 19

Tilt device to make a selection.

Pain...

Bathroom...  Thirsty...

Something else...

[Show Algorithm] [Note] [Next Mode]

Have you had this pain before?

Yes, it's familiar...

BACK

No, it's new pain

Show Algorithm  Note  Next Mode

Where am I?

BACK  I am not comfortable

I want someone...

[Show Algorithm] [Note] [Next Mode]

Suction

BACK  Hot/Cold

Re-position

[Show Algorithm] [Note] [Next Mode]

ADAPTIVE, MULTIMODAL COMMUNICATION SYSTEM FOR NON-SPEAKING ICU PATIENTS

CROSS-REFERENCE TO RELATED APPLICATIONS

This application is the U.S. national phase of and claims priority to PCT/US2016/066081, filed Dec. 12, 2016, which claims priority to and the benefit of U.S. provisional patent application Ser. No. 62/266,558, filed Dec. 11, 2015, which application is incorporated herein by reference in its entirety.

FIELD OF THE INVENTION

The invention relates to communication systems in general and particularly to a communication system that is suitable for use by a non-speaking individual.

BACKGROUND OF THE INVENTION

Patents who are intubated in a hospital setting, such as an ICU, have difficulty communicating with other people, such as doctors and nurses. Various methods of communication, such as the use of a pad of paper and a writing instrument such as a pen or pencil, have been used under such circumstances.

Also known in the prior art is Patak et al., U.S. Pat. No. 6,422,875, issued Jul. 23, 2002, which is said to disclose a device for communicating with a voice-disabled patient, which includes, generally, a housing having a display surface, indicia on the display surface that may be utilized by the patient to indicate the status and needs of the patient, and a marker that the patient may use to convey his or her status and needs to a third party. One embodiment includes a clipboard having two eraser-board surfaces and an erasable marker connectable to the clipboard. Another embodiment includes a lap-sized housing for a computer and a touch pad-activated screen. In both embodiments, the indicia includes a series of descriptive words and phrases indicating the status and needs of the patient, and graphical representations of anterior and posterior views of a human body with descriptive words correlating to common symptoms of specific parts of the body.

Also known in the prior art is Chinese Pat. No CN 201130476 Y, titled "ICU patient-nursing communication card", granted Oct. 8, 2008, which is said to disclose an ICU nurse-patient communicating card, comprising a faceplate and a transparent plastic sheet covering the faceplate, which is characterized in that a plurality of catchwords or images, which are respectively arranged at both sides of the faceplate and specified according to the mentality and physiology of patients and environment, can accurately reflect the characteristic information of the patient, so the nurse can attend on the patients with good pertinence, purposiveness and scientificity, and provide a safe and best service for the patient with less error. The ICU nurse-patient communicating card has the advantages of simple structure, easy production, and effective and convenient use.

Also known in the prior art is Harris, U.S. Pat. No. 7,880,722, issued Feb. 1, 2011, which is said to disclose a communicator device which allows improved functions. The communicator device may have real movable keys which are reconfigured when the device is used in different orientations. In a sideways orientation, the device has a rectangular aspect ratio which is wider than it is tall. And in that sideways orientation, the buttons are reconfigured to the orientation they would normally have. The communicator device may also be reoriented into the other position, in which case the assignment and the indication on the buttons is also correspondingly changed. The communicator device may have a projector to project videos, and the communicator device may be able to retrieve numbers and e-mails to be used for communications from a repository on the Internet or from a search engine on the Internet.

Also known in the prior art is Traughber et al., U.S. Pat. No. 8,183,987, issued May 22, 2012, which is said to disclose a method and system for advanced patient communication. According to one embodiment, a computer-implemented method comprises providing a patient communication device through which a patient communicates a first message from a hospital bed. The first message is received at a central processing server. The first message is processed to identify an urgency level of the message. One or more additional messages are generated based on the first message. The one or more additional messages are transmitted to specific health care provider devices of specific health care providers who are expected to respond to the patient.

Also known in the prior art is Traughber et al., European Patent Application Publication No. EP 2660744 A1, titled "A method and system for advanced patient communication", published Nov. 8, 2013, which is said to disclose a method and system for advanced patient communication. According to one embodiment, a computer-implemented method comprises providing a patient communication device through which a patient communicates a first message from a hospital bed. The first message is received at a central processing server. The first message is processed to identify an urgency level of the message. One or more additional messages are generated based on the first message. The one or more additional messages are transmitted to specific health care provider devices of specific health care providers who are expected to respond to the patient.

There is a need for a communication apparatus and method that improves on existing methods of communication by non-speaking patients.

SUMMARY OF THE INVENTION

According to one aspect, the invention features a communication system, comprising: a cylindrical hand operated input device configured to accept input conveyed by mechanical motion and configured to convert the input conveyed by mechanical motion into an electrical signal, the cylindrical hand operated input device having at least one mechanical input device operable by hand and having at least one electrical signal output port; a general purpose programmable computer that is configured to operate under the control of a set of instructions recorded in a non-volatile manner on a machine readable medium, the general purpose programmable computer having at least one input port configured to receive the electrical signal from at least one electrical signal output port of the cylindrical hand operated input device, the general purpose programmable computer configured to interpret and process the received signal and to generate a response signal at a response signal output port; and a display device configured to receive the response signal from the response signal output port and to provide an output signal in at least one of visual and audible form to a user of the communication system.

In one embodiment, the cylindrical hand operated input device comprises a key.

In another embodiment, the cylindrical hand operated input device comprises a tilt device.

In yet another embodiment, the cylindrical hand operated input device comprises a device that is configured to accept a press motion.

In still another embodiment, the general purpose programmable computer is integrated with the cylindrical hand operated input device.

In a further embodiment, the general purpose programmable computer is mechanically separate from the cylindrical hand operated input device.

In yet a further embodiment, any two of the cylindrical hand operated input device, the general purpose programmable computer and the display device are connected by a wired connection.

In an additional embodiment, any two of the cylindrical hand operated input device, the general purpose programmable computer and the display device are connected by a wireless connection.

In one more embodiment, the cylindrical hand operated input device comprises a structure that holds the cylindrical hand operated input device in proximity to a hand of a user.

In still a further embodiment, the communication system is configured to display prompts to a user in a first language, and to display user responses in a second language.

According to another aspect, the invention relates to a method of making a communication system, comprising the steps of: providing a cylindrical hand operated input device configured to accept input conveyed by mechanical motion and configured to convert the input conveyed by mechanical motion into an electrical signal, the cylindrical hand operated input device having at least one mechanical input device operable by hand and having at least one electrical signal output port; providing a general purpose programmable computer that is configured to operate under the control of a set of instructions recorded in a non-volatile manner on a machine readable medium, the general purpose programmable computer having at least one input port configured to receive the electrical signal from at least one electrical signal output port of the cylindrical hand operated input device, the general purpose programmable computer configured to interpret and process the received signal and to generate a response signal at a response signal output port; providing a display device configured to receive the response signal from the response signal output port and to provide an output signal in at least one of visual and audible form to a user of the communication system; and interconnecting the cylindrical hand operated input device, the general purpose programmable computer and the display device to make the system operational.

According to another aspect, the invention relates to a method of using a communication system, comprising the steps of: providing a cylindrical hand operated input device configured to accept input conveyed by mechanical motion and configured to convert the input conveyed by mechanical motion into an electrical signal, the cylindrical hand operated input device having at least one mechanical input device operable by hand and having at least one electrical signal output port; providing a general purpose programmable computer that is configured to operate under the control of a set of instructions recorded in a non-volatile manner on a machine readable medium, the general purpose programmable computer having at least one input port configured to receive the electrical signal from at least one electrical signal output port of the cylindrical hand operated input device, the general purpose programmable computer configured to interpret and process the received signal and to generate a response signal at a response signal output port; providing a display device configured to receive the response signal from the response signal output port and to provide an output signal in at least one of visual and audible form to a user of the communication system; interconnecting the cylindrical hand operated input device, the general purpose programmable computer and the display device to make the system operational; and allowing a first person having a speech impediment to operate the system to communicate in a non-spoken manner with a second person.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 19 is an image of a user screen used to orient a patient.

DETAILED DESCRIPTION

Figure 1:
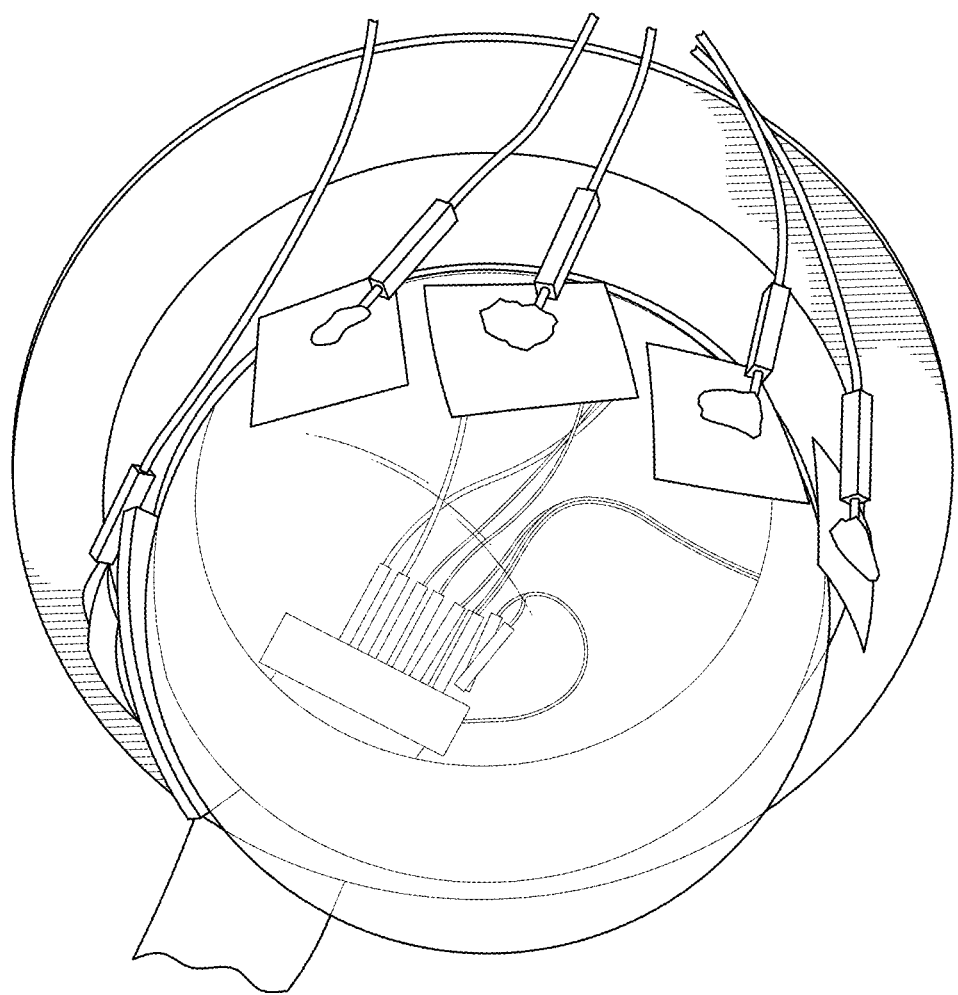
FIG. 1 is an image of an embodiment of a hand operated device.

In the present invention a patient who is unable to communicate by spoken methods communicates directly with a medical professional, such as a doctor or a nurse in the patient's room. In various preferred embodiments, the device is configured to adjust automatically not only to the content of the message but to the patient's method of use and the patient's abilities.

By way of example, a patient who is intubated may not be able to communicate by spoken or oral methods because of the tube that has been placed in the patient's mouth and throat. There is a need under such conditions for the patient to be able to express his or her feelings, needs and desires to medical personnel.

In the examples presented, the language used is English, and the examples use visual displays. However, it should be understood that in various embodiments the devices described herein can be programmed to operate using any language that the patient (also referred to as "the user") understands. For example, a user may be fluent or comfortable in a language other than English, such as Spanish, French, Italian, Russian, Chinese, or any other language. In some embodiments, the display can include an enunciator, such as a speaker, so that the display can also be expressed as language that can be sensed by hearing, so that a patient or user who is visually impaired can interact with and operate the device using commands issued as sounds.

In one embodiment, there is provided a multi-use system for communication, having at least one hardware component, and at least one available software interface, that best meets the needs of ICU patients and care team members. In one embodiment, the system comprises a handheld unit, responsive to multiple types of tactile input, which will be accessible to a patient lying in bed; and a tablet displaying visual output and producing audio output situated in proximity to the bed, so tatthe display is visible to (and can be heard by) the patient and others in the room.

In one embodiment, the patient navigates the user interface on the tablet using the handheld device to produce visual and audible output from the tablet and tactile feedback from the handheld unit. The handheld unit component responds dynamically to patient use patterns. In some embodiments, the "squeeze" duration threshold can be adjusted (lengthened or shortened) based on sensing of upper motor neuron deficits that impair relaxation. In other embodiments; the amount of motion required to operate a joystick or other hand operated input device may be adjustable to accommodate weakness or proprioception deficits.

The communication system will allow communication about topics of ICU relevance, including a patient request for nurse/nurse assistance, a patient request for presence of family members, a patient request for information on the patient's location and/or situation, and a patient request for assistance, for example help with suctioning the patient's mouth/traceostomy or increasing the patient's moisture level.

The system will be accessible to a physically restrained patient. A recent study of 40 American hospitals showed rates of physical restraint use for ventilated patients ranging from 10% to 92%. Since one characteristic of the ICU environment is that delirium is an issue for many patients, patients may often find themselves restrained to avoid self-extubation if they have experienced bouts of delirium in the present ICU visit or in the past, or if they are at high risk of delirium. A device that is accessible to patients who are restrained will greatly increase the likelihood of its use.

Both the hardware and software components of the system are adaptable to the patient's physical deficits or impairments, and can be programmed to accommodate a preferred language of each of a patient and a medical professional, so that communication between the patient and the medical professional (or between the patent and others, such as family members) can be conducted.

By way of example, a patient who is fluent in a first language and a medical professional (or another person) who is fluent in a second different language may communicate by the simple expedient that the display may be programmed to display simultaneously (or to display to two monitors, one in the first language and the second in the second language) in two languages, or may be programmed to enunciate in two languages in succession. This can be implemented using a simple bilingual dictionary, or using bilingual pre-arranged display selections.

This device is designed to fit the needs of patients who may have a wide range of deficits (such as tremor, swelling, weakness, or nerve damage) with multifactorial causes, including patients' underlying conditions and the exacerbation of critical illness. It is therefore advantageous that the system be able to address the fact that patients' needs will vary between patients, and may vary for a single patient over the course of a day.

The software operates initially in a simple fashion. The software can be more sophisticated, in ways that can be initiated by either the user or the medical professional (e.g. nurse).

The initial "resting" state of the device requires an activation signal to begin a communication session. In some embodiments, this activation, or start, signal can be a "push down" or similar initial gesture or motion (e.g., a motion similar to pushing a button, or a key press on a controller).

FIG. 1 is an image of an embodiment of a hand operated device. The device illustrated in FIG. 1 has five pressure switches, each one positioned to be conveniently accessed by one finger of a patient's hand.

Figure 2:
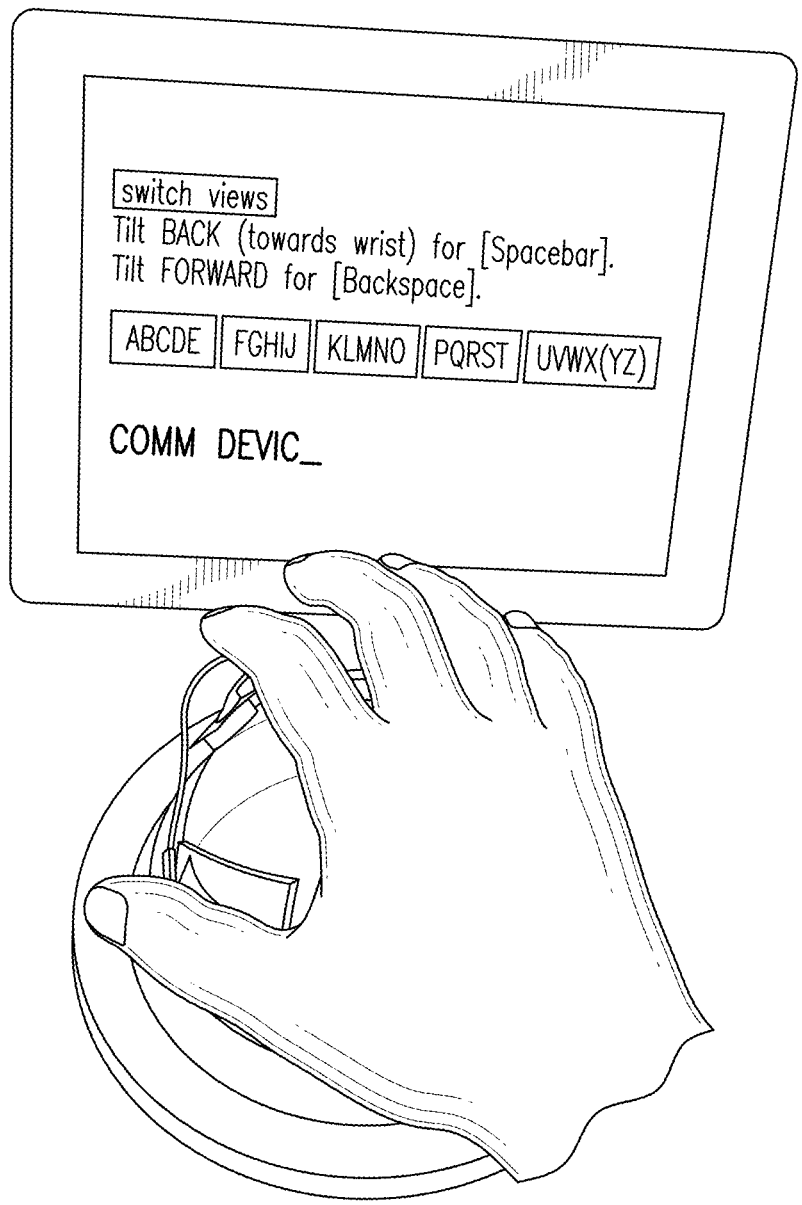
FIG. 2 is an image of a first screenshot of a display of the device, and also shows a hand in position on the hand operated device.

FIG. 2 is an image of a first screenshot of a display of the device, and also shows a hand in position on the hand operated device.

Figure 3:
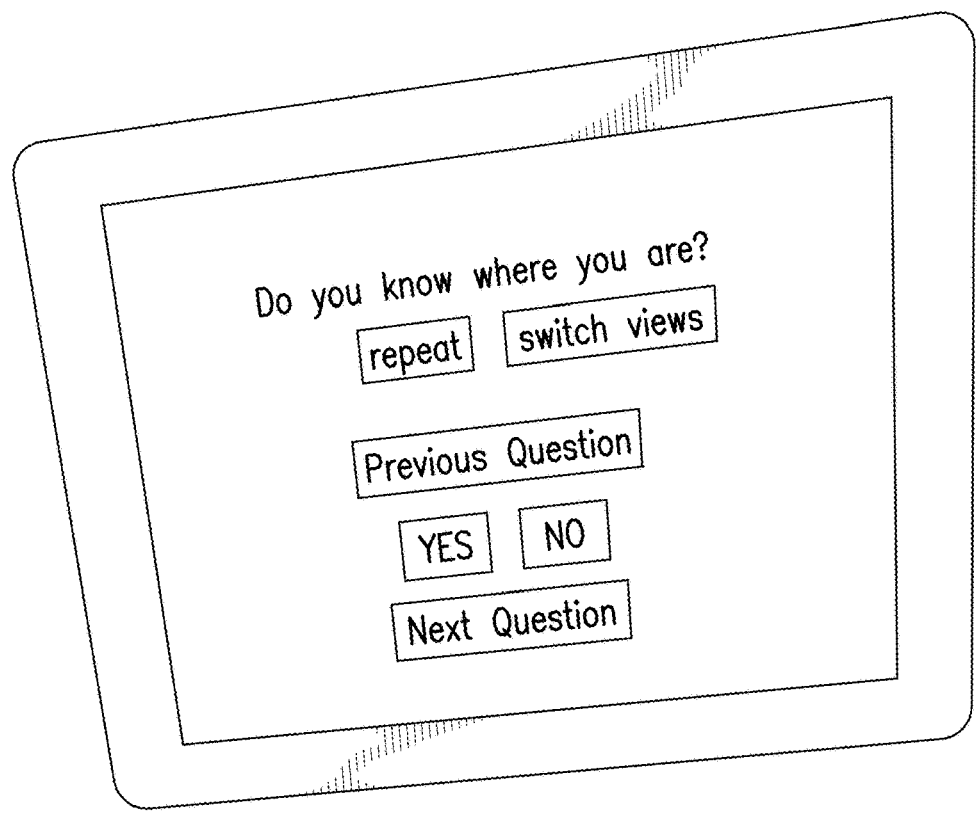
FIG. 3 is an image of a second screenshot of the display.
Figure 3:
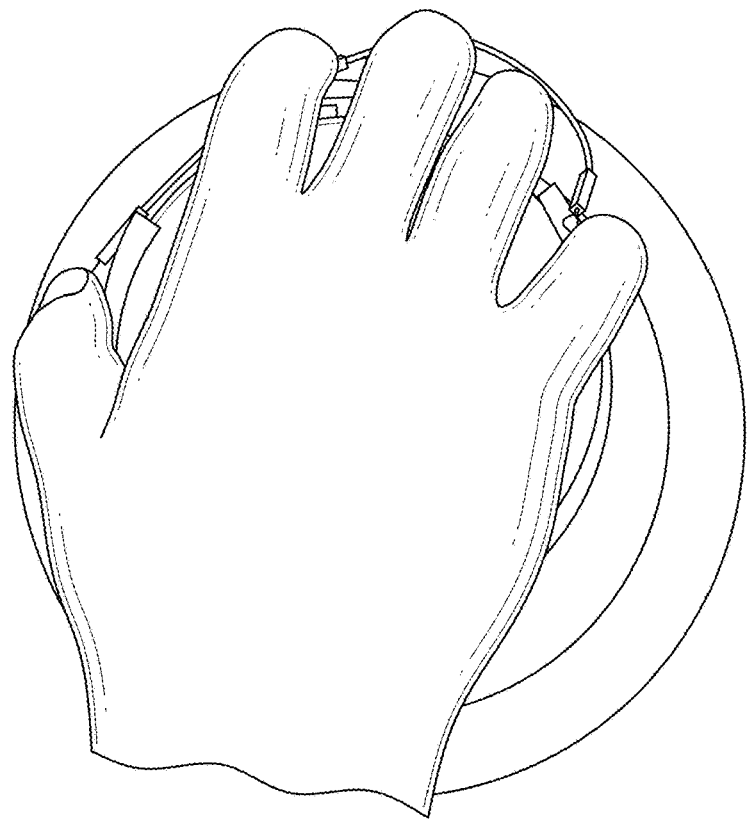

FIG. 3 is an image of a second screenshot of the display.

In one embodiment, such as that shown in FIG. 1 through FIG. 3, the device operates by the action of a patient pressing one or more finger controlled switches in a sequence of presses. As used herein, a sequence of presses is used to describe one or more pressing actions that a patient may perform to cause the system to operate.

Figure 4:
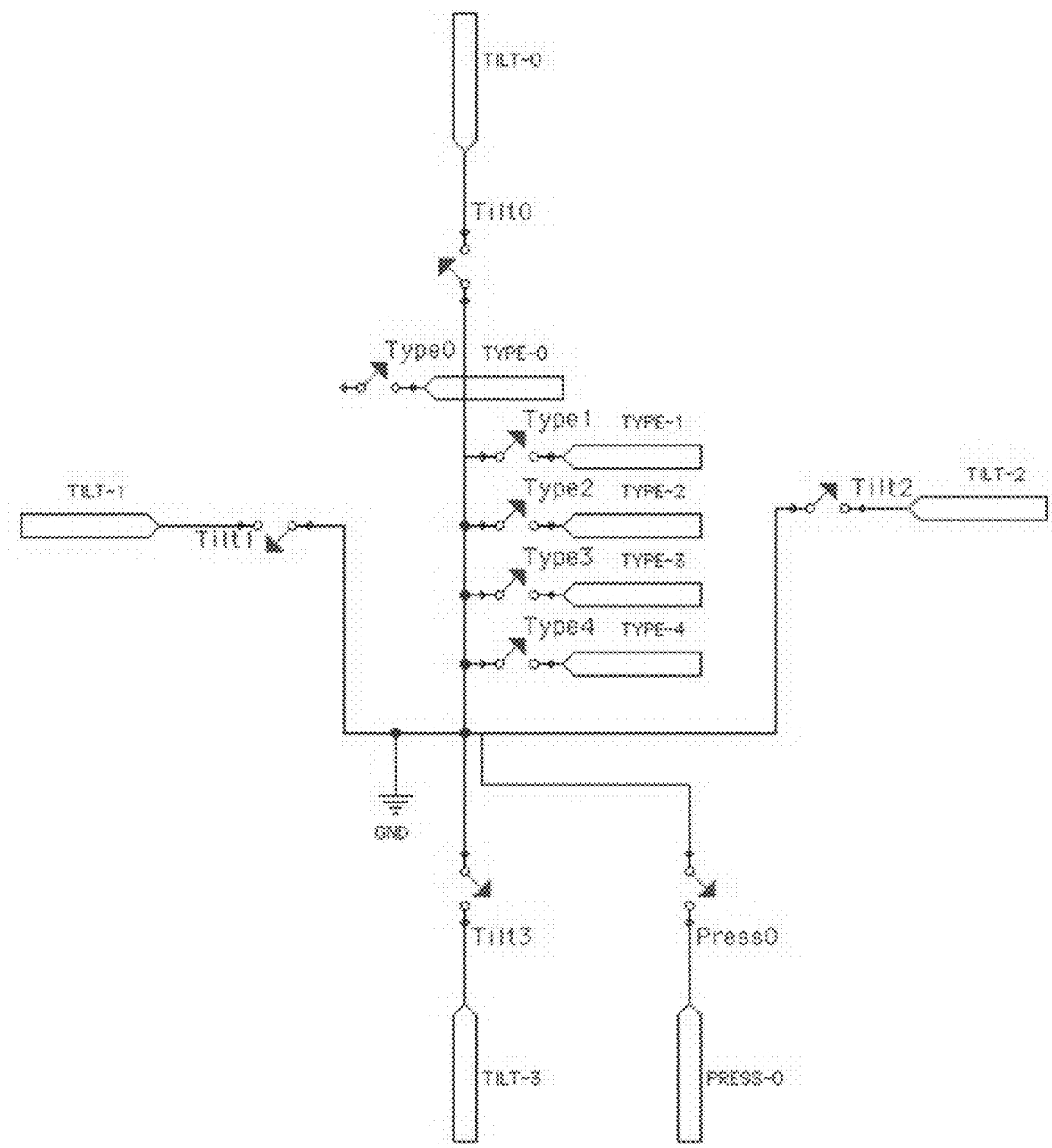
FIG. 4 is a schematic diagram of one embodiment of the circuitry of the device.
Figure 5:
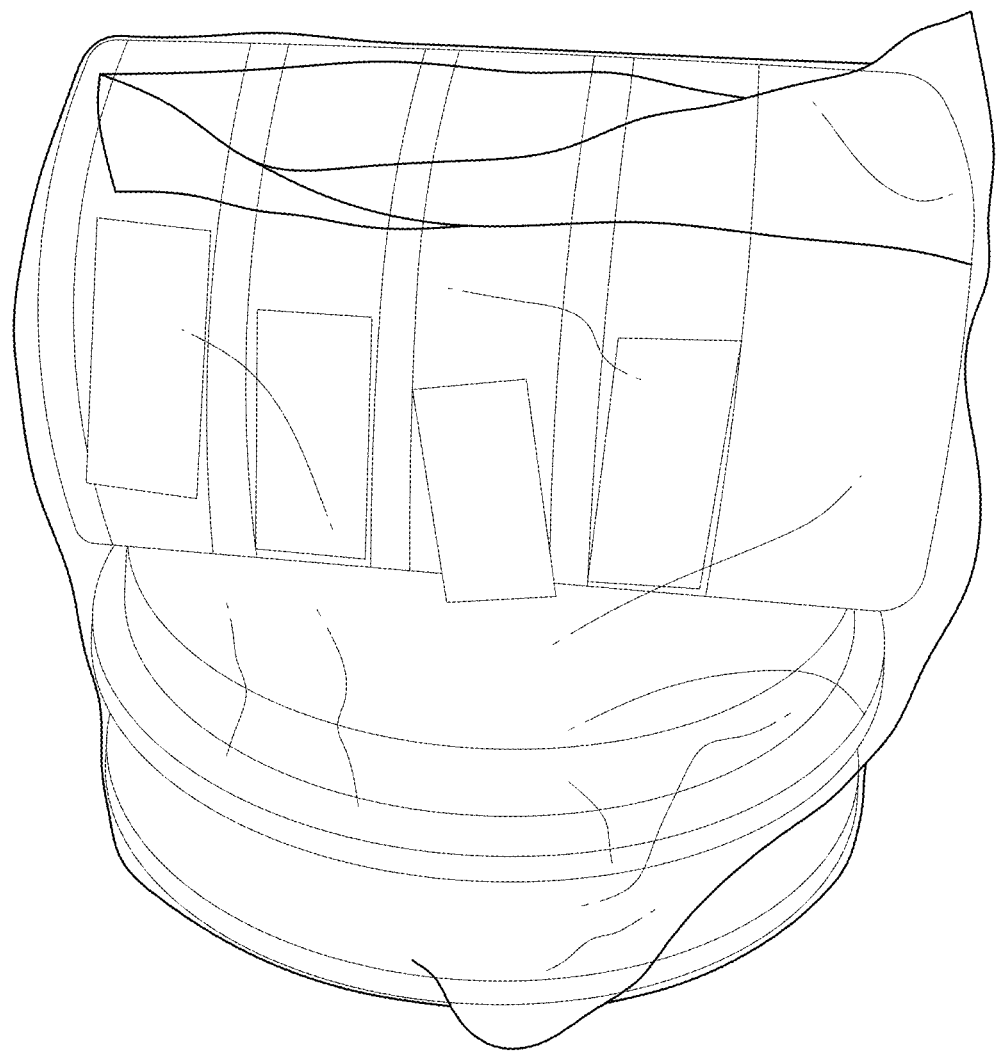
FIG. 5 is an image of a cylindrical device showing pressure switches that are accessible by the user's fingertips.
Figure 6:
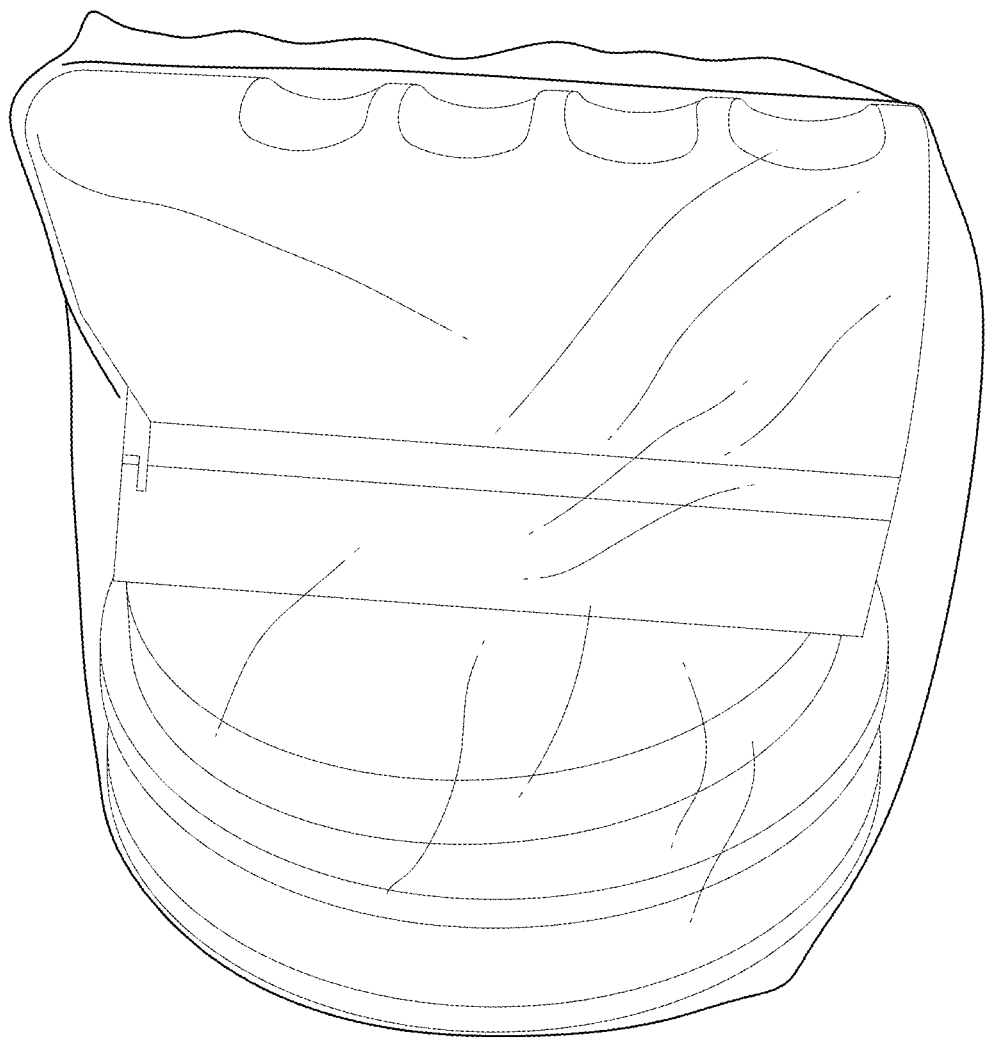
FIG. 6 is an image of a cylindrical device showing the area upon which the user's palm is placed.
Figure 7:
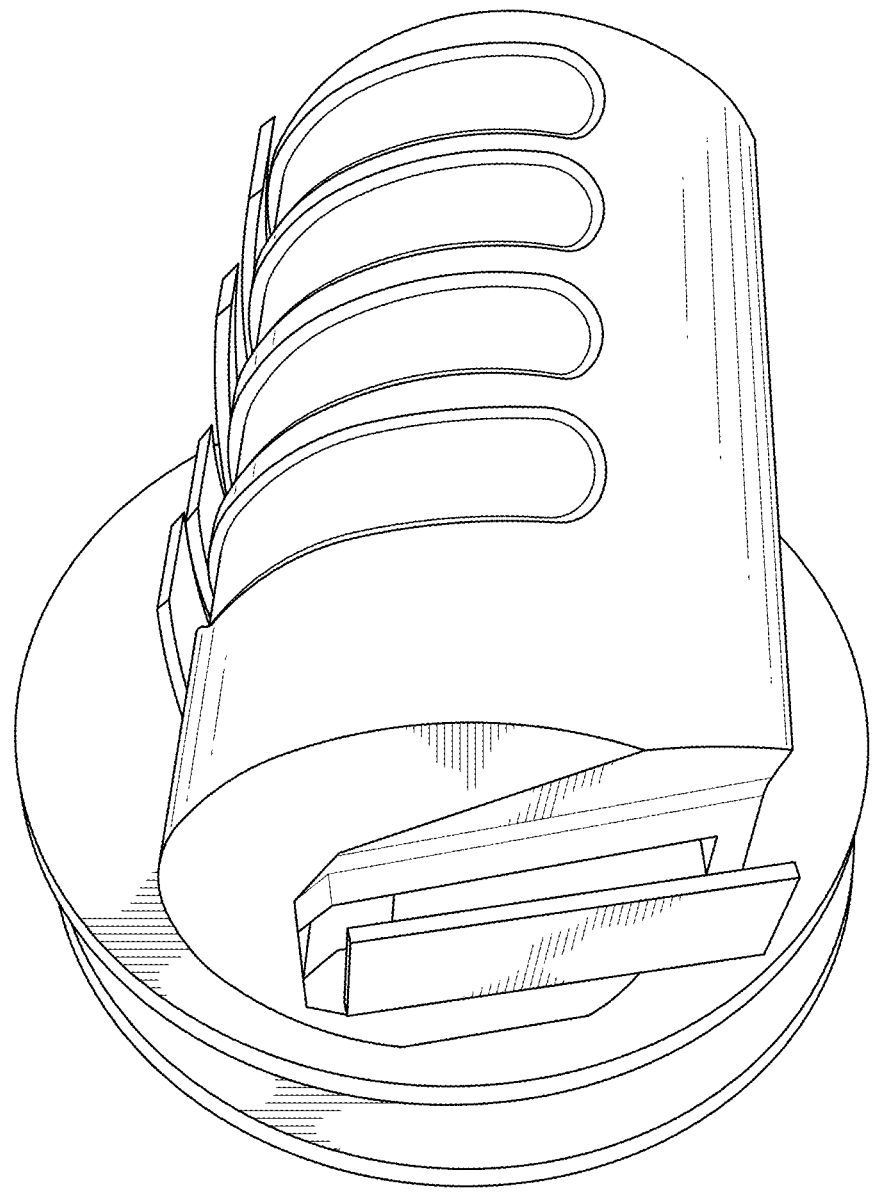
FIG. 7 is an image of an embodiment of a cylindrical device showing where the user's fingers and thumb contact switches.
Figure 8:
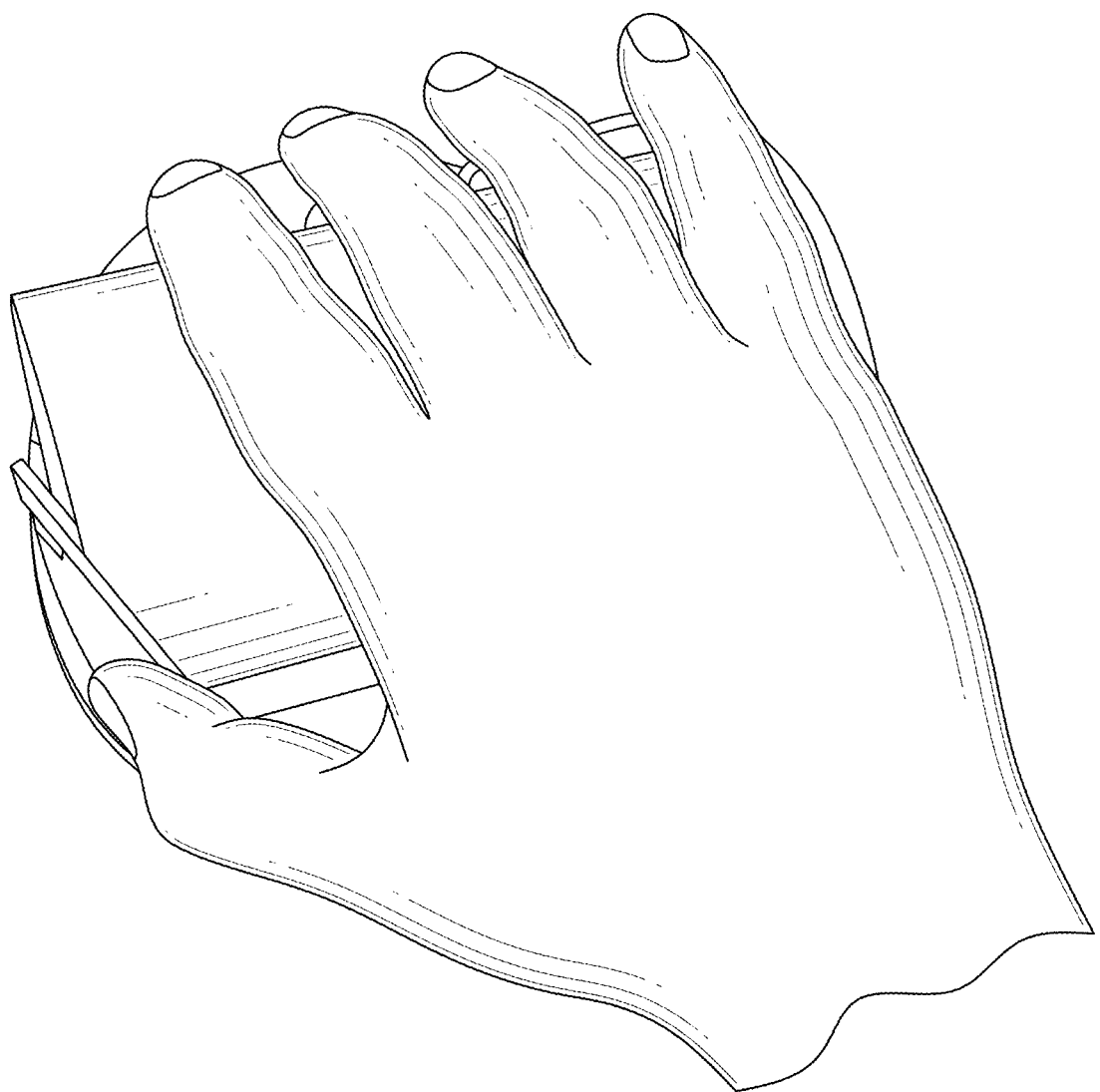
FIG. 8 is an image of an embodiment of a cylindrical device showing where the user's fingers and thumb contact switches, including showing the user's hand in position to operate the device.
Figure 9:
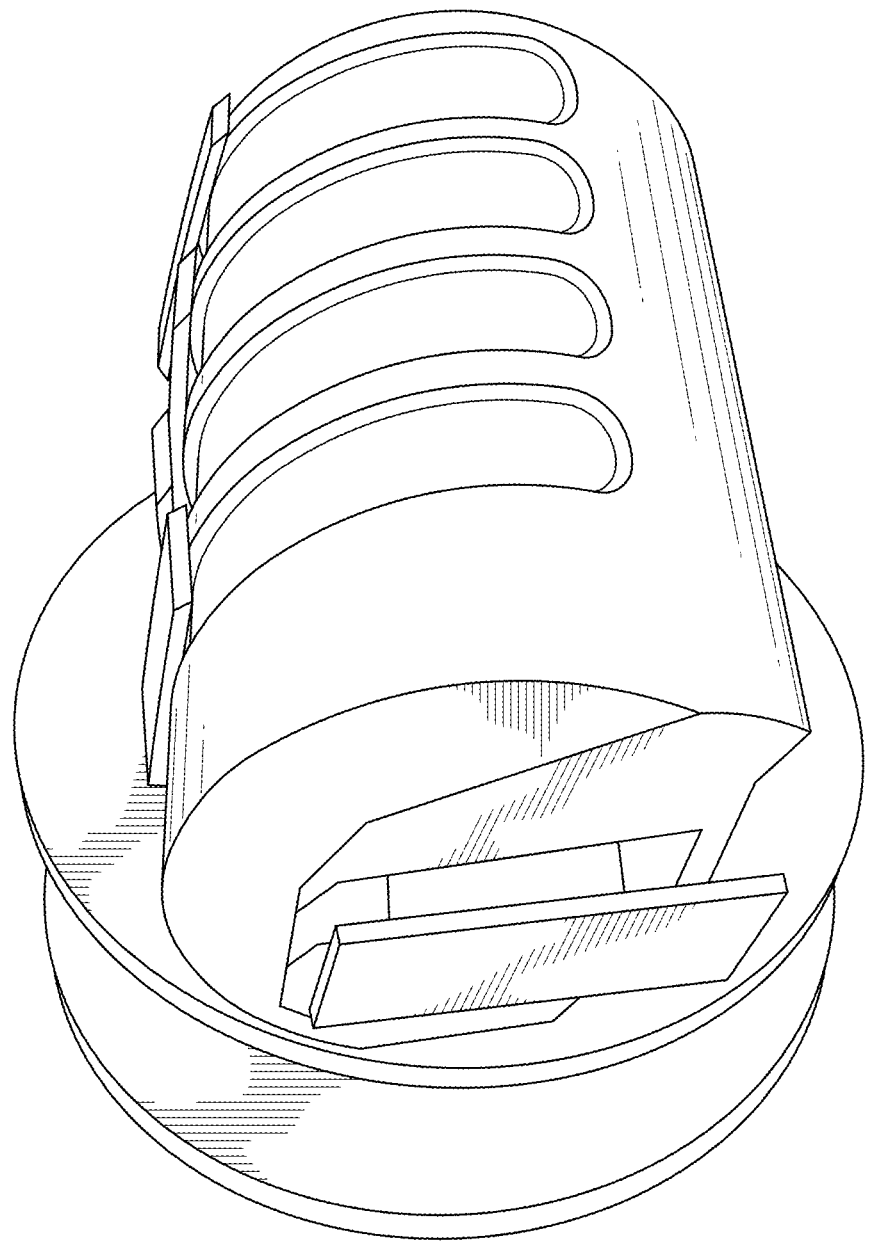
FIG. 9 is an image of another embodiment of a cylindrical device showing where the user's fingers and thumb contact switches.
Figure 10:
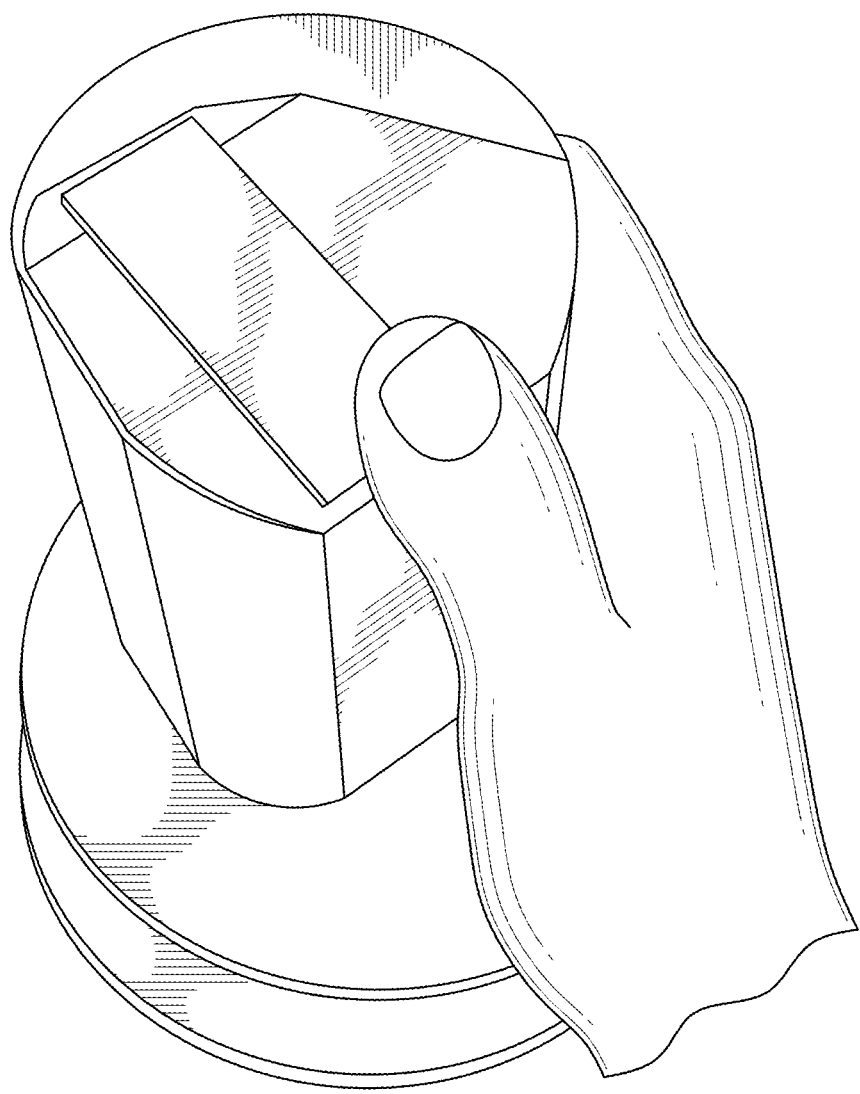
FIG. 10 is an image of a third embodiment of a cylindrical device showing where the user's fingers and thumb contact switches, including showing the user's hand in position to operate the device.

FIG. 4 is a schematic diagram of one embodiment of the circuitry of the device. The embodiment in FIG. 4 is that of a device that can provide four tilt directions (labeled TILT-0, TILT-1, TILT-2 and TILT3 in the schematic) and that can also provide five key press (or "typing") operations (labeled TYPE-0, TYPE-1, TYPE-2, TYPE-3 and TYPE-4) each activated by a digit of a patient's hand. In one embodiment, the tilt directions include a "neutral" central position (which in some embodiments is provided by using a spring loaded tilt device, such as a joystick-like device) and four tilt positions, such as "East-West-North-South" positions (e.g., four tilt directions that are aligned bi-directionally along two orthogonal tilt axes). The "neutral" position can include a motion such as a "pressing down" motion to give a signal in the neutral position (labeled PRESS-0).

The circuitry illustrated in FIG. 4 is in communication with a general purpose programmable computer so that the motions made by the patient can be sensed and interpreted as inputs to the communication system. In one embodiment, the general purpose programmable computer operates under a set of instructions, such as the code provided herewith as txt files, which set of instructions is recorded in a non-volatile manner on a machine readable medium.

In some embodiments, the general purpose programmable computer and the set of instructions recorded in a non-volatile manner on a machine readable medium are provided within the hand operated input device.

In some embodiments, the general purpose programmable computer and the set of instructions recorded in a non-volatile manner on a machine readable medium are provided in a device separate from the hand operated input device.

In one embodiment, the system employs a hand operated input device that accepts input instructions using pressure switches operated by respective ones of the digits on a person's hand. FIG. 5 through FIG. 10 illustrate embodiments of such hand operated input device devices.

In one embodiment, the hand operated input device accepts input in "tilt-in-compass directions" manner, allowing the user to scroll through a list of questions or to move between keys on a virtual keyboard. If the user appears sufficiently physically able and/or the nurse indicates that it is appropriate, the same hardware may also function as a "keyboard", allowing each finger to be used to pick out letters individually and facilitating typing-based communication. In some embodiments a typing mode may be faster to operate than a tilting mode.

Figure 11:
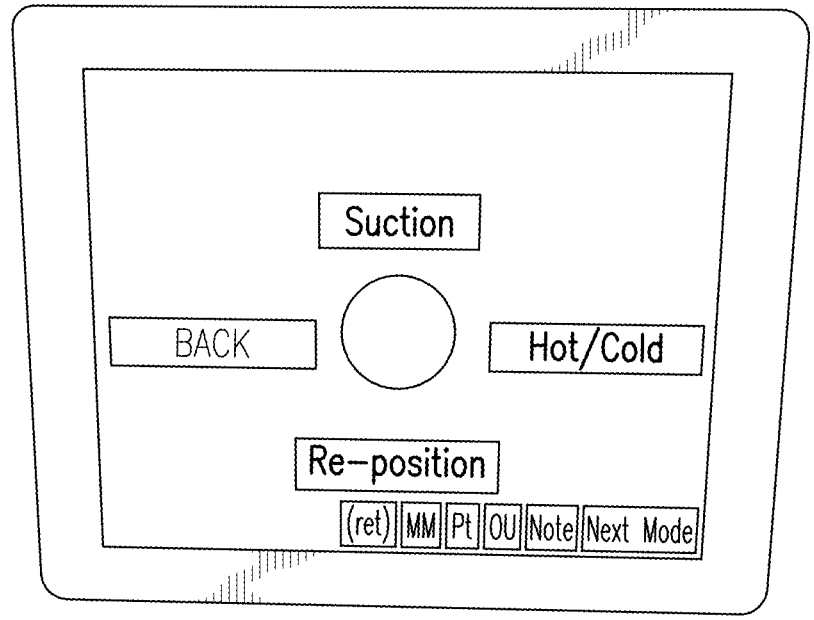
FIG. 11 is an image of a fourth embodiment of a cylindrical device that operates in tilt mode, including a display.
Figure 11:
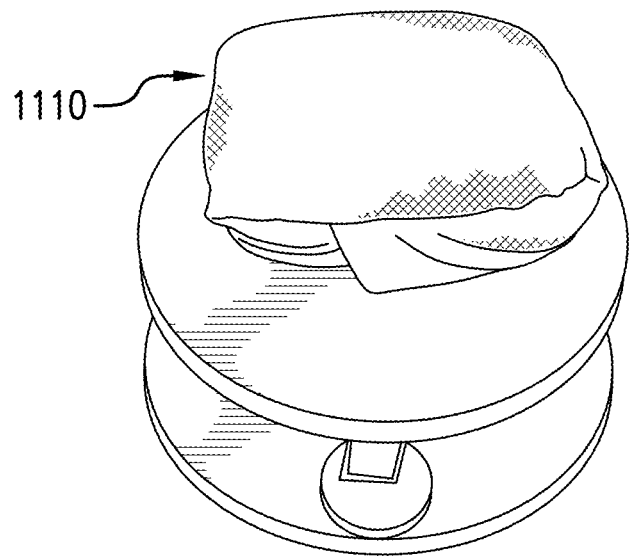

FIG. 11 is an image of a fourth embodiment of a cylindrical device 1110 that operates in tilt mode, including a display. The image shown is in the "neutral" position. In this embodiment, rather than pressing down in the neutral position, the patient is required to squeeze the handle to indicate a selection.

Figure 12:
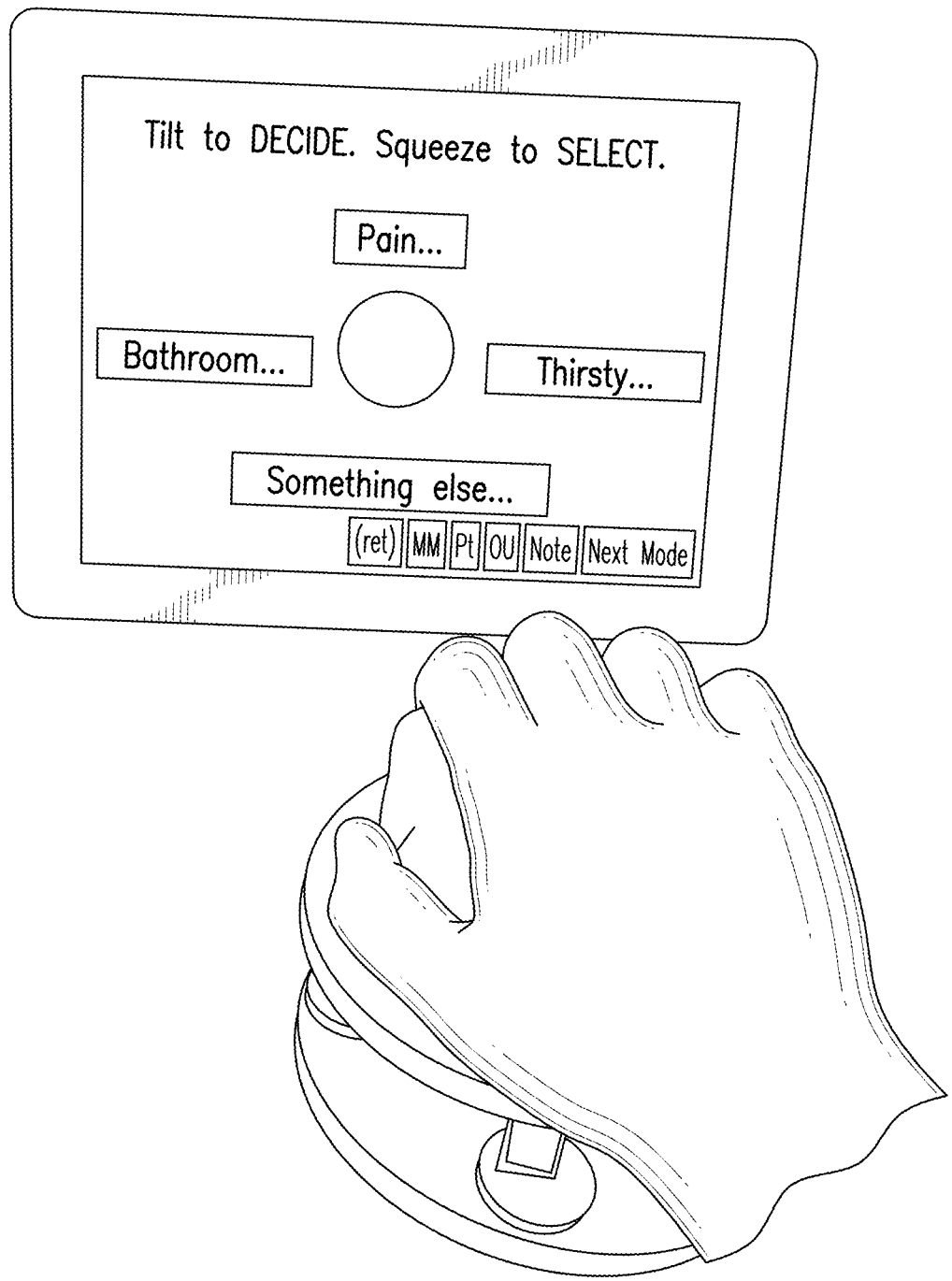
FIG. 12 is another image of a fourth embodiment of a cylindrical device that operates in tilt mode, including a display, with a user's hand in the starting position used to operate the device.

FIG. 12 is another image of a fourth embodiment of an approximately cylindrical device that operates in tilt mode, including a display, with a user's hand in the starting position used to operate the device. In FIG. 12, the four tilt directions correspond to "pain", "thirsty", "bathroom", and "something else".

Figure 13:
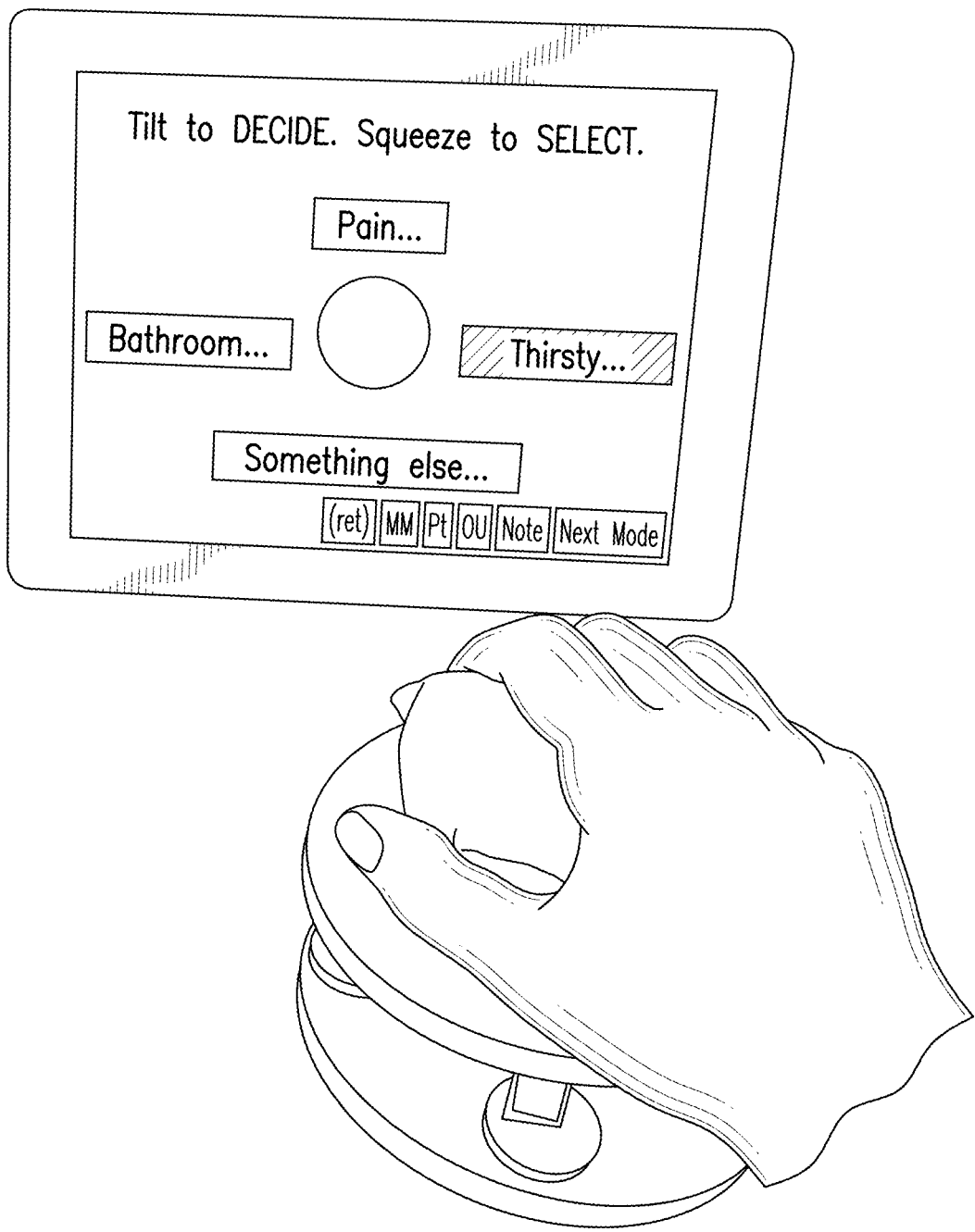
FIG. 13 is an image of the fourth embodiment of a cylindrical device that operates in tilt mode, illustrating a tilt motion with a selection of an action.

FIG. 13 is an image of the fourth embodiment of an approximately cylindrical device that operates in tilt mode, illustrating a tilt motion with a selection of an action (here "thirsty").

Figure 14:
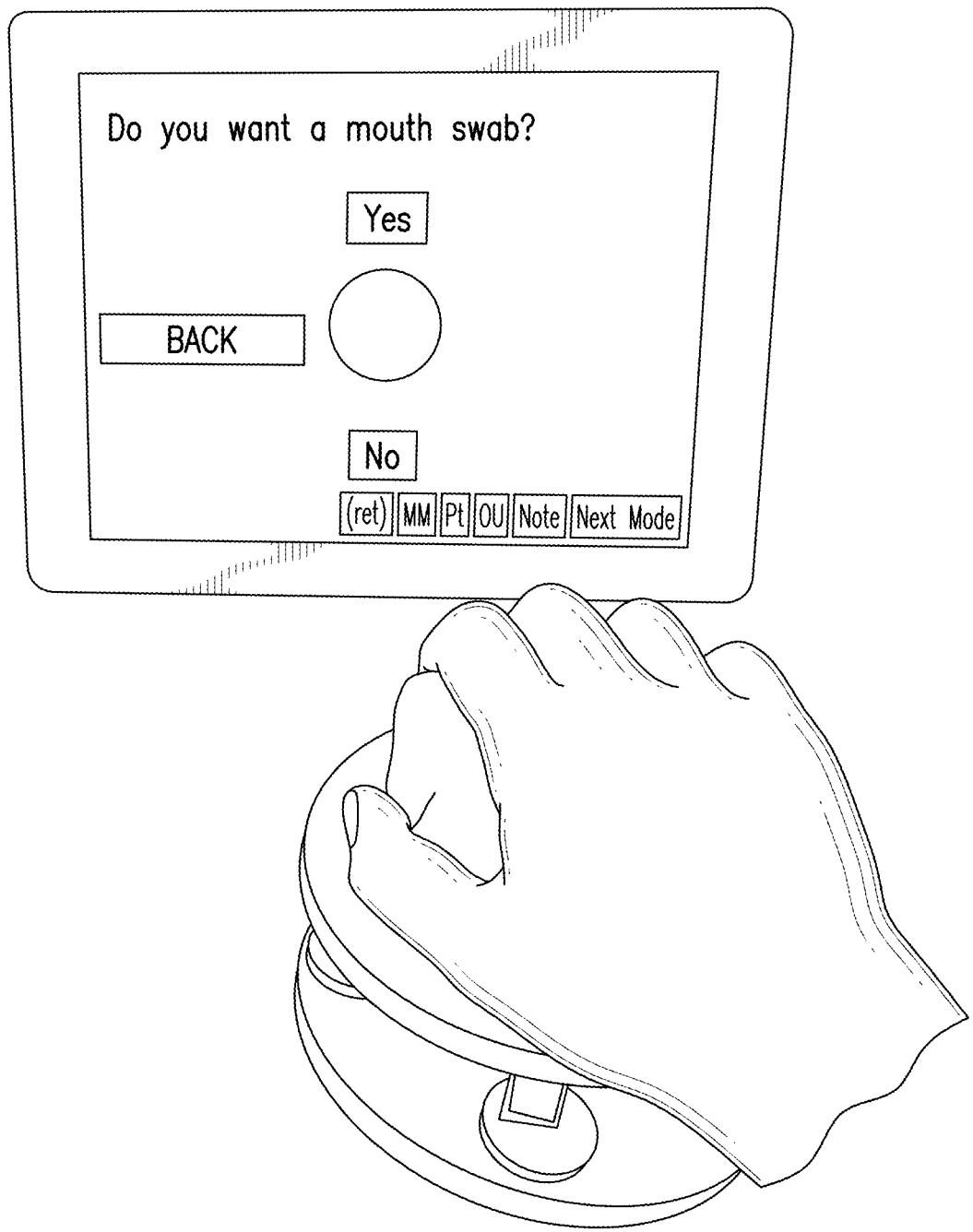
FIG. 14 is an image of the fourth embodiment of a cylindrical device that operates in tilt mode, after the user has selected the option "thirsty" illustrated in FIG. 13.

FIG. 14 is an image of the fourth embodiment of a cylindrical device that operates in tilt mode, after the user has selected the option "thirsty" illustrated in FIG. 13. The patient can ow select among the choices "yes", "no", and "back" (e.g., return to the previous screen).

Figure 15:
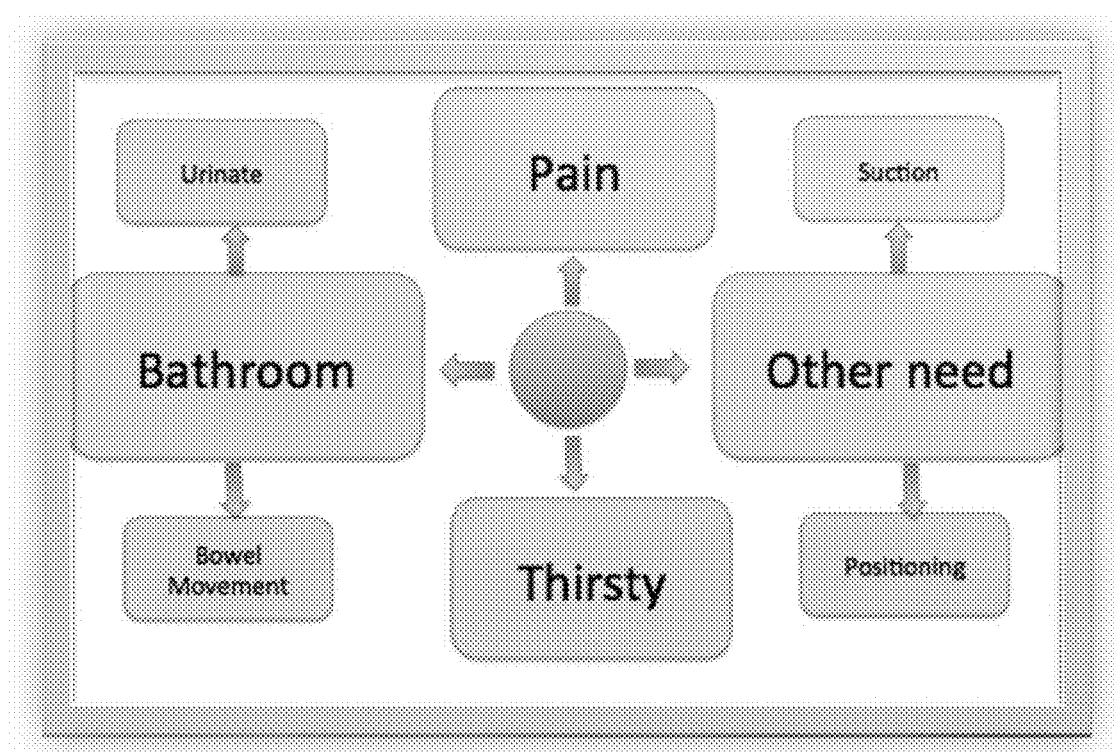
FIG. 15 is a schematic image of a display embodiment in which the tilt choices are presented as a "word cloud."

FIG. 15 is a schematic image of a display embodiment in which the tilt choices are presented as a "word cloud." The "word cloud" comprises a series of nodes with identifiers that represent specific choices, set out in a simply connected hierarchical sequence, which a patient may navigate. In the embodiment illustrated in FIG. 15, the patient uses the input in tilt mode to navigate from the central (circular) node to one of the four nodes directly connected to the central node. Providing a press or a squeeze signal chooses that node, from which the patient can navigate to another node directly connected to the selected node, and then make a further selection by a press or squeeze action. While only two levels of interconnected nodes are shown in FIG. 15, it should be understood that any number of levels of connected nodes may be provided, as long as the possible node choices may be discerned by the user.

Figure 16:
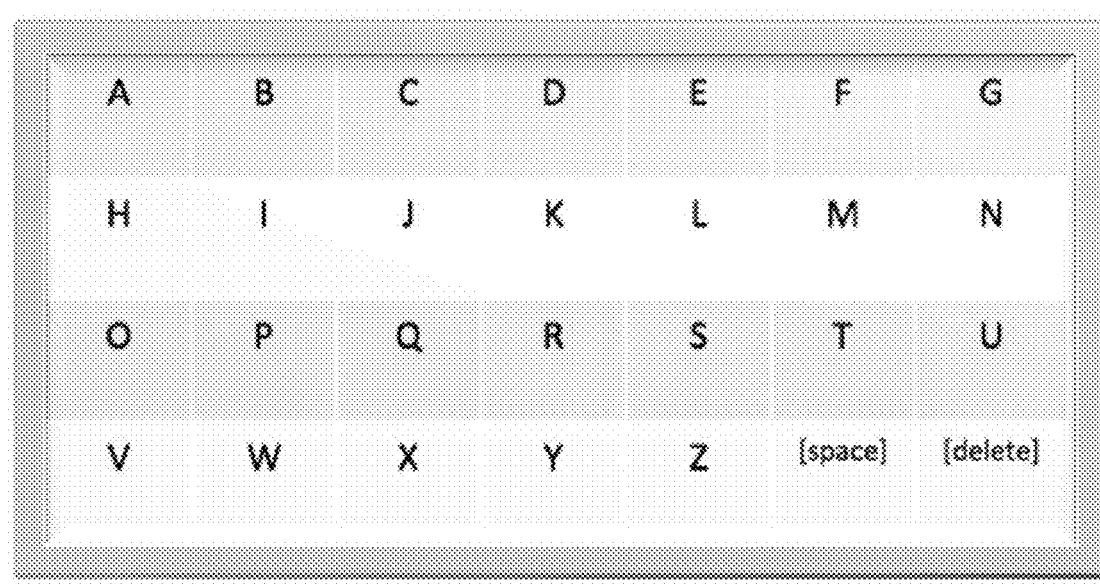
FIG. 16 is an image of a display embodiment in which a keyboard is presented to a user.

FIG. 16 is an image of a display embodiment in which a keyboard is presented to a user. The user can navigate the keyboard by tilting the input device handle in any of four orthogonal directions, thereby successively moving from letter to letter until a desired letter is reached. An activation signal (a press or a squeeze) then selects that letter. In some embodiments the hand operated input device can include a tilt sensor that operates in at least two axial directions, so that tilting the entire hand operated input device serves the same function as moving a joystick handle.

Figure 17:
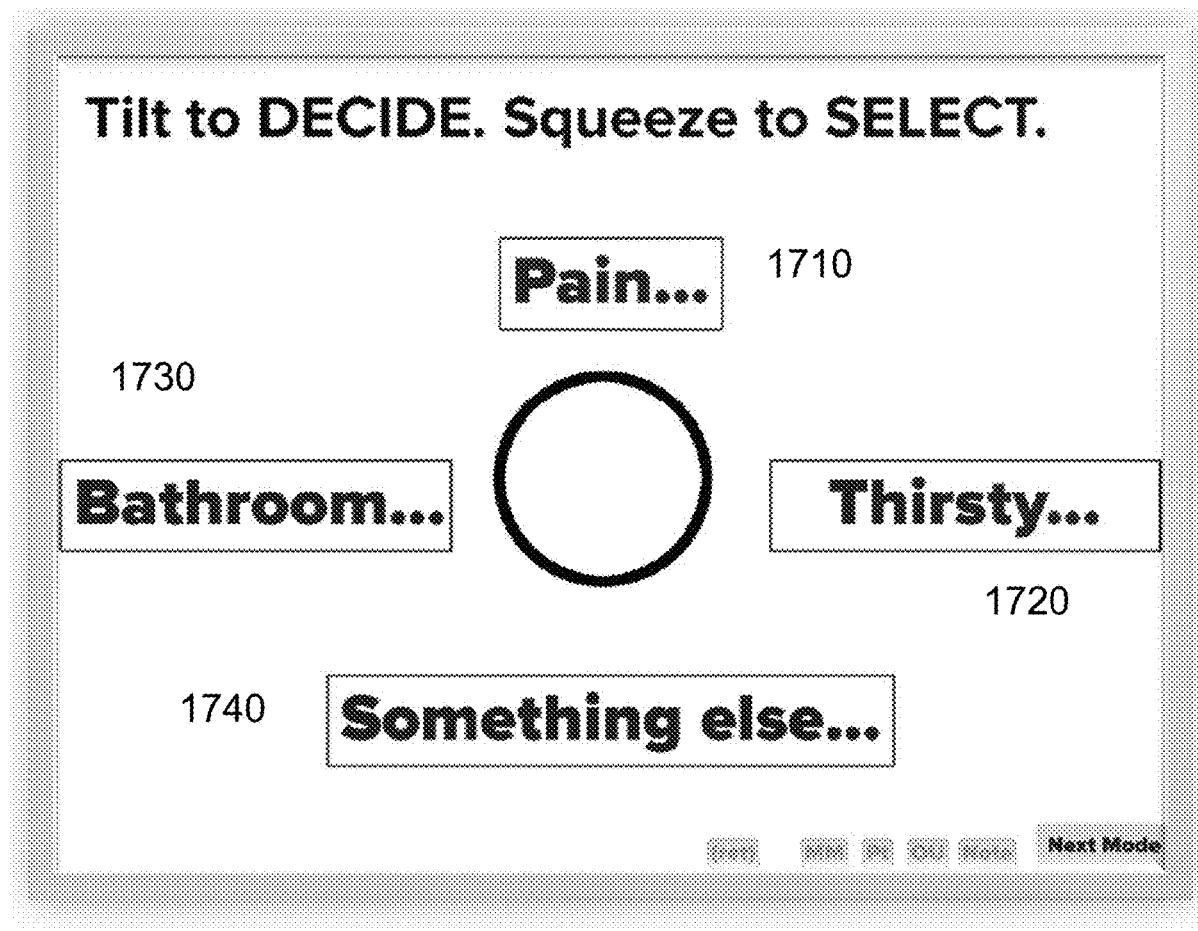
FIG. 17 is an image of a display embodiment in which each selection is visually distinguishable from the other selections.

FIG. 17 is an image of a display embodiment in which each selection is visually distinguishable from the other selections. In FIG. 17, the four choices are indicated as "pain" 1710, "thirsty" 1720, bathroom" 1730, and "something else" 1740.

Figure 18:
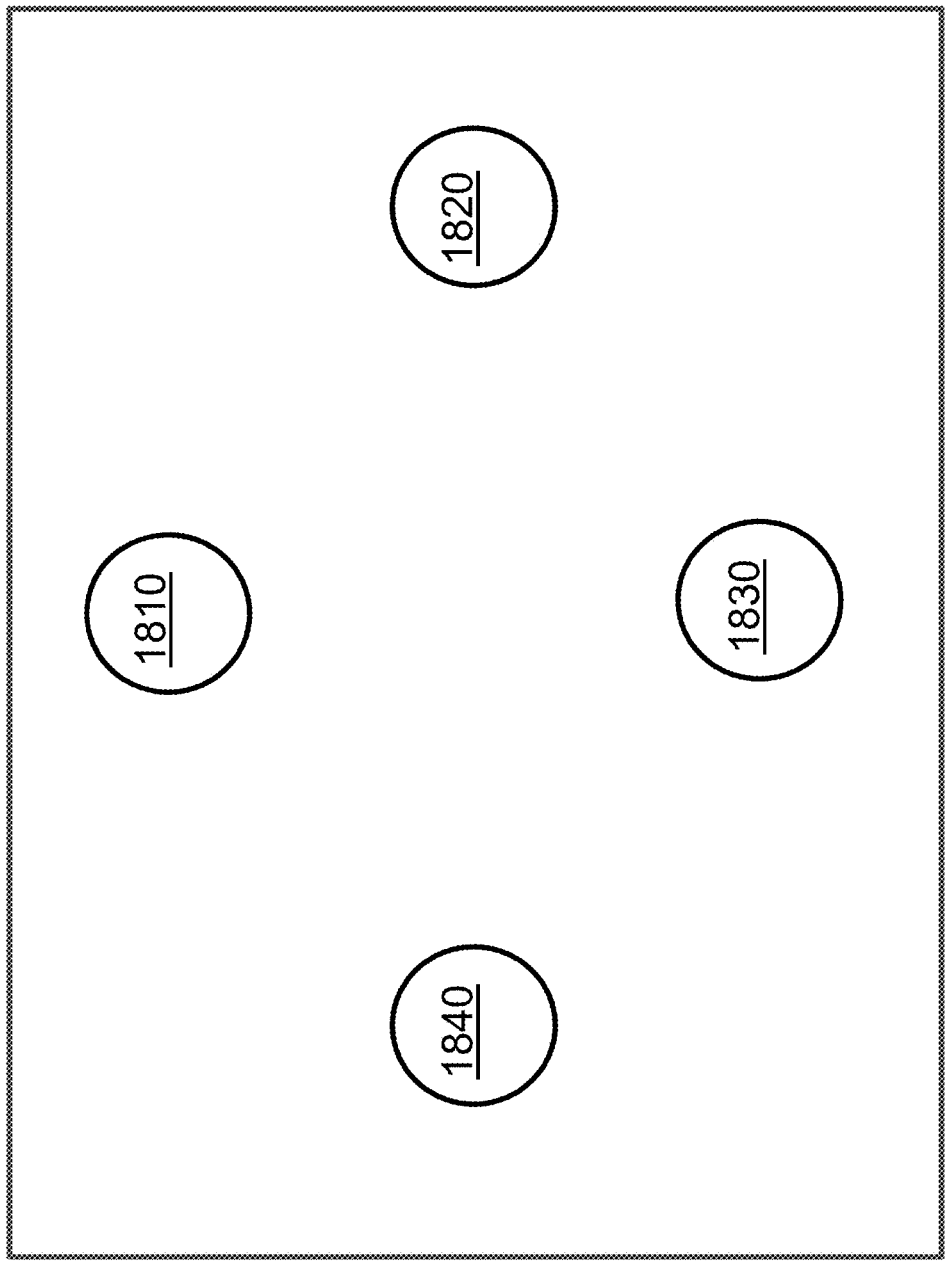
FIG. 18 is an image of a keypad embodiment in which each of four keys is visually distinguishable from the other keys, and corresponds to one of the selections illustrated in FIG. 17.

FIG. 18 is an image of a keypad embodiment in which each of four keys (1810, 1820, 1830, 1840) is visually distinguishable from the other keys, and corresponds to one of the selections illustrated in FIG. 17. For example, in one embodiment the display item 1710 and the key 1810 might be colored red, and the other respective pairs of display items and keys (1720 and 1820, 1730 and 1830, and 1740 and 1840) might be other colors, such as blue, green and yellow, so that a user can make the proper associations.

In the embodiments of FIG. 17 and FIG. 18, the simplified display and keys will be more convenient than direct tablet use for some patients, such as patients who are unfamiliar with interfaces such as are found on tablet computers, smart phones, and the like.

FIG. 19 is an image of a user screen used to orient a patient. For example, in the embodiment shown, the patient is identified, and his or her location and the current date and time are displayed.

Figure 20:
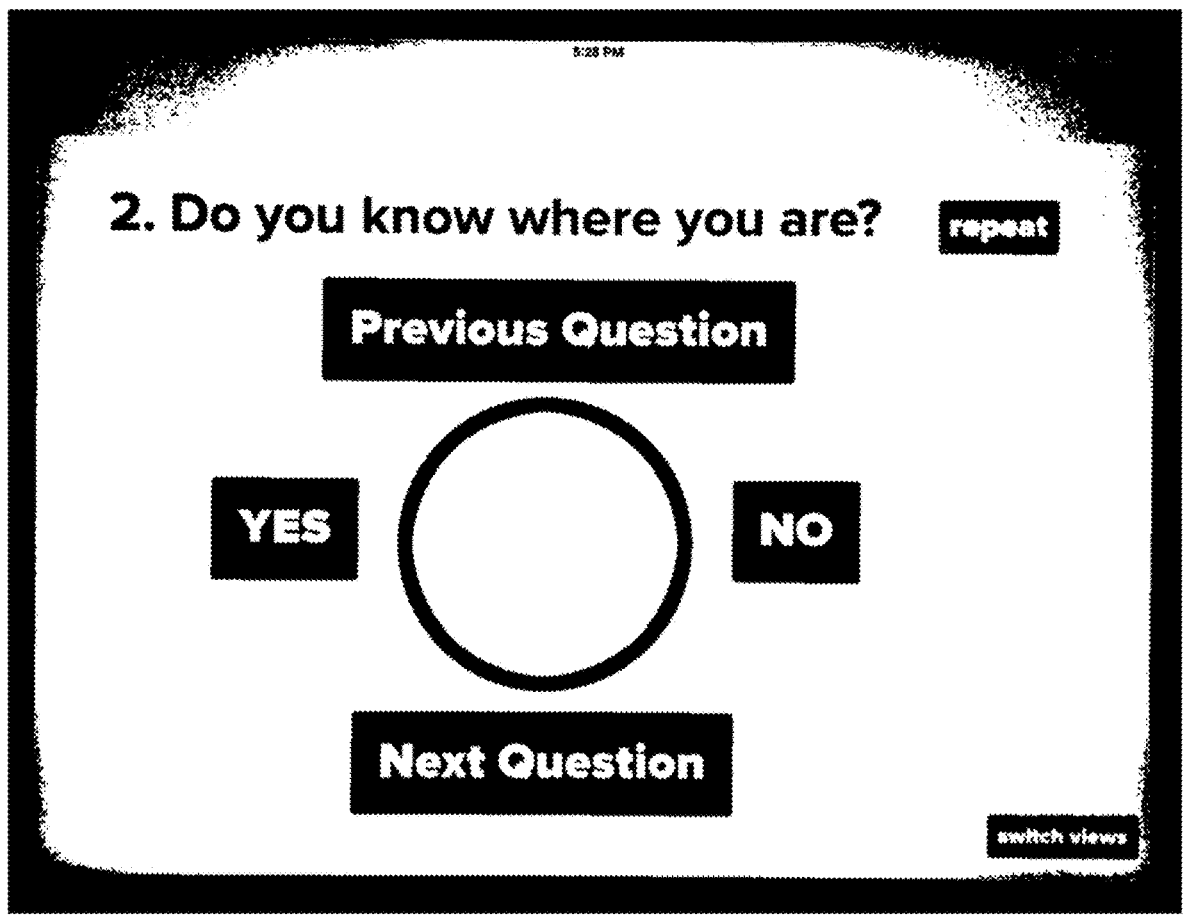
FIG. 20 is an image of a user screen that operates in tilt mode.

FIG. 20 is an image of a user screen that operates in tilt mode. The user screen allows the patient to provide input to the question that is displayed.

Figure 21:
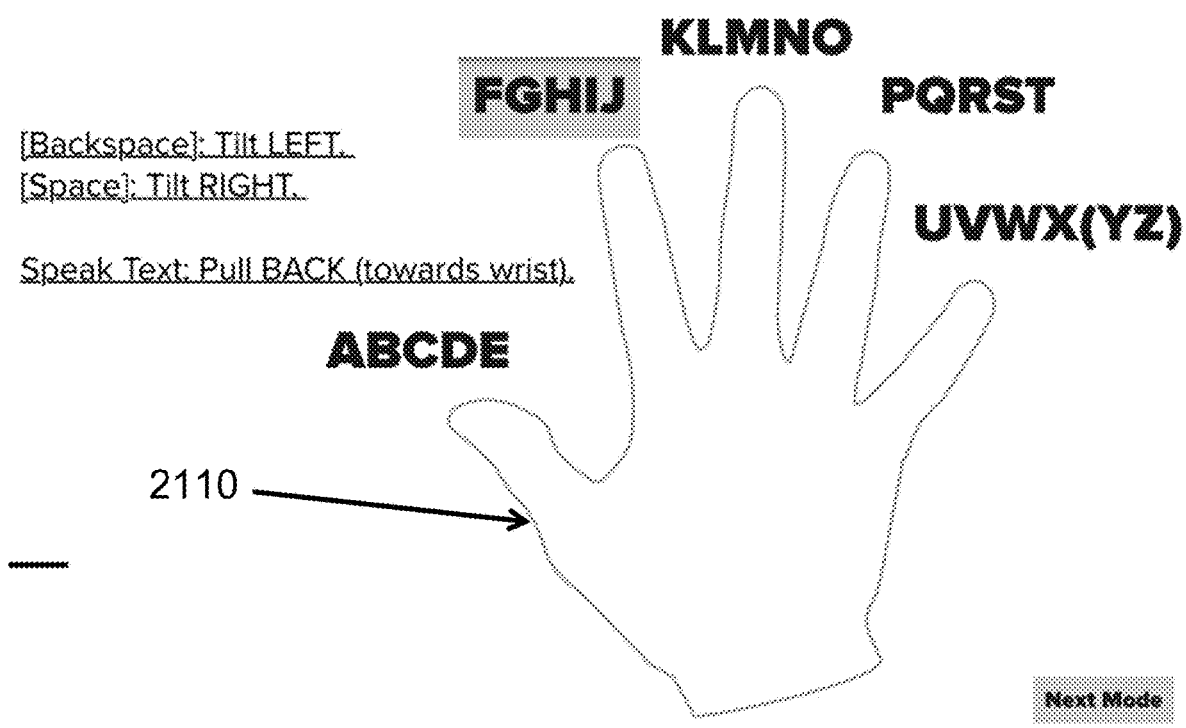
FIG. 21 is a diagram that illustrates the operation in "type" mode in which the user is starting to type the word "Hello" by choosing the group that include the letter "H".

FIG. 21 is a diagram that illustrates the operation in "type" mode in which the user is starting to type the word "Hello" by choosing the group that include the letter "H". The user selects a group of letters and then gives an activation command (e.g., a press or a squeeze). This mode of operation is most conveniently and preferably performed with a device that allows each of the patient's five digits to activate a respective switch. In FIG. 21 there is shown schematically a glove-like structure 2110 into which a user can place one or more fingers of a hand so as to temporarily attach the input device to one's hand, which make activating the device more readily accomplished even in the absence of a surface upon which to rest the hand operated input device.

Figure 22:
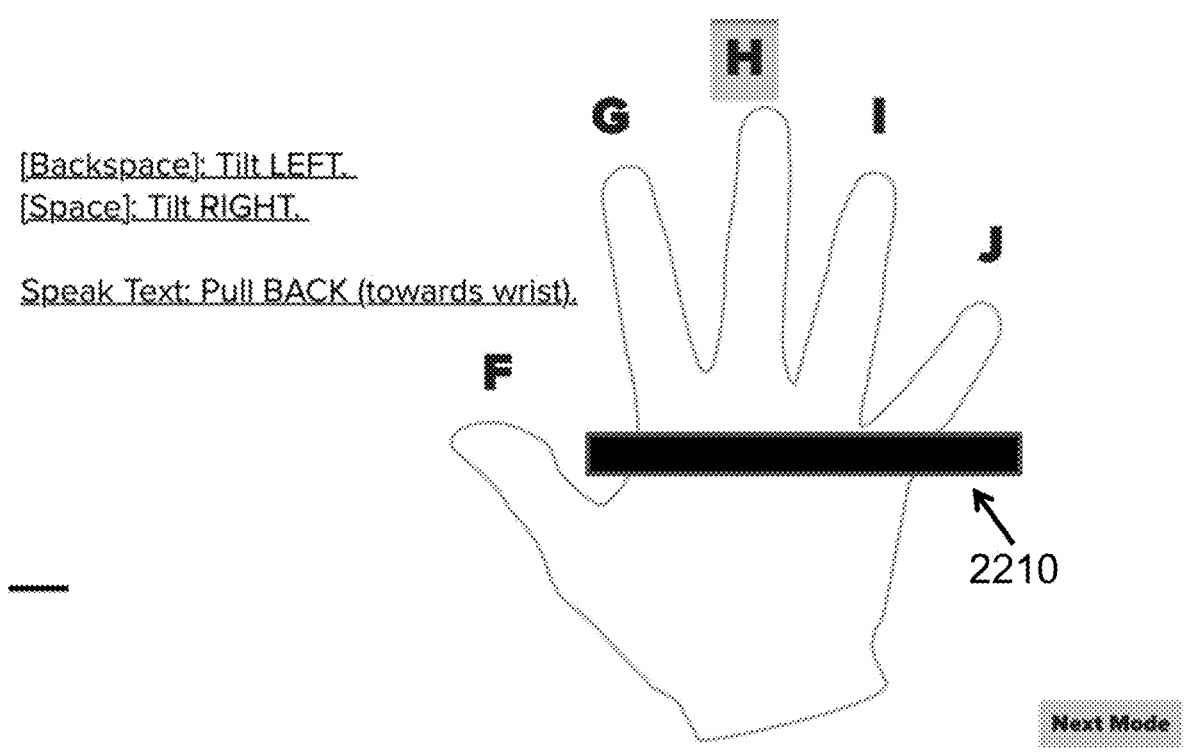
FIG. 22 is a diagram that illustrates the operation in "type" mode in which the user is starting to type the word "Hello" by choosing the letter "H".

FIG. 22 is a diagram that illustrates the operation in "type" mode in which the user is starting to type the word "Hello" by choosing the letter "H". Having selected the group including the letters "F", "G", "H", "I", and "J", the user can now select an individual letter by pressing the appropriate switch. In another embodiment, as illustrated in FIG. 22 there is shown schematically a strap-like structure 2210 under which a user can place one or more fingers of a hand so as to temporarily attach the input device to one's hand, which make activating the device more readily accomplished even in the absence of a surface upon which to rest the hand operated input device.

Figure 23:
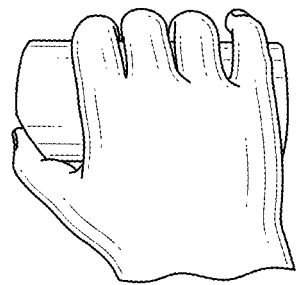
FIG. 23 is an image of an embodiment of a user screen that employs tilt.

FIG. 23 is an image of an embodiment of a user screen that employs tilt.

Figure 24:
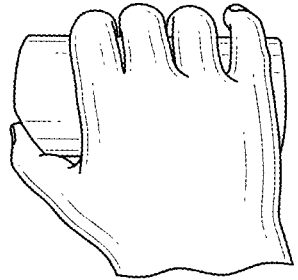
FIG. 24 is an image of a user screen that appears when the user has selected the "pain" option in FIG. 23.

FIG. 24 is an image of a user screen that appears when the user has selected the "pain" option in FIG. 23.

Figure 25:
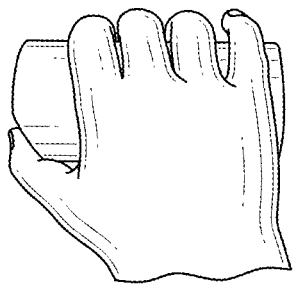
FIG. 25 is an image of a user screen that appears when the user has selected the "something else" option in FIG. 23.

FIG. 25 is an image of a user screen that appears when the user has selected the "something else" option in FIG. 23.

Figure 26:
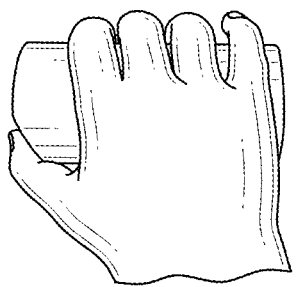
FIG. 26 is an image of a user screen that appears when the user has selected the "I am not comfortable" option in FIG. 25.

FIG. 26 is an image of a user screen that appears when the user has selected the "I am not comfortable" option in FIG. 25.

Figure 27:
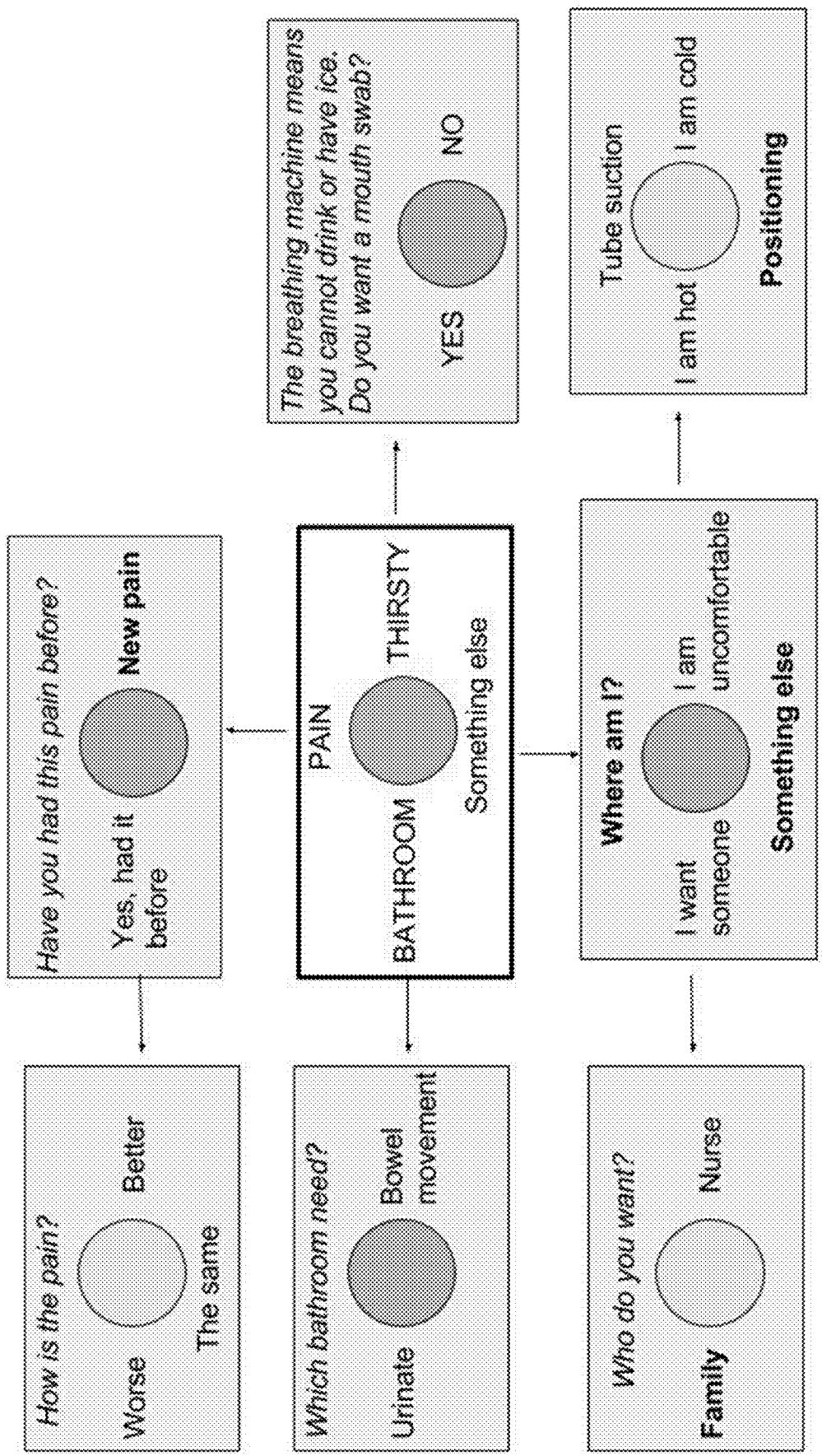
FIG. 27 is a schematic of one embodiment of screens that can be displayed to a user in the tilt mode of operation.

FIG. 27 is a schematic of one embodiment of screens that can be displayed to a user in the tilt mode of operation. The operation of the embodiment of FIG. 27 is analogous to that of FIG. 15. One navigates from the central position of the central display to select a new display, and one then manipulates the choices in that display and so forth until one reaches the choice that is desired.

In some embodiments the system will produce synthesized speech output. The speech output may be provided by a speaker within the display, or may be provided by a separate speaker.

The device can produce tactile feedback, e.g. such as producing vibration when an action is initiated and/or completed. Haptic interfaces are commercially available that can provide vibration when required. In addition, an audible signal such as a buzz may be provided to indicate that the vibration is occurring. Examples of such feedback devices are often built into modern cellular telephones. Technology for people with disabilities has been shown to benefit from the addition of tactile feedback.

The system is fully hygienic, as is appropriate for a medical setting such as an ICU. Every part of the device that may come into contact with patients preferably should be either disposable or sanitizable. In some embodiments, it may be preferred that some components are sanitizable/coverable (with a disposable cover). In some embodiments, it may be preferred that a component is disposable (such as the handheld component if it only comprises a set of switches and not a general purpose programmable computer nor a machine readable memory).

It is believed that he invention improves upon prior art in three significant ways that are relevant for ICU patients:

The system and its components are designed to be accessible for interaction initiation by patients who are restrained, which is common in an ICU context (since delirium is frequent and patients who become even briefly delirious may remove their breathing tube)

The system and its components are designed to accommodate physical deficits which may vary between patients (so that the same hardware can be used by several patients with different variations on tremor, weakness, and/or motor/sensory nerve damage) by dynamically adjusting in terms of input interpretation. In some embodiments, a patient who rapidly toggles the device "joystick" back and forth repeatedly may have tremor. In some embodiments, until the joystick is held to one side for a period longer than a minimum time interval, the input is not accepted. Alternatively, until the patient activates a switch, the inut is not accepted.

In some embodiments, for a patient who may exhibit upper motor neuron damage leading to spasticity, the device should not register any new input until the joystick component moves back to the center position.

The system and its components are designed to accommodate several different physical interaction methods. By way of example, a patient who is only able to push on the device may use it as just a nurse call button; a patient who is able to move it in the four compass directions, but not type, may choose from one of two answer choices or may move among the letters of a keyboard shown on screen; and patients with advanced physical dexterity may use capacitive finger touch areas in order to use the device as a keyboard.

Applications

It is expected that the invention will be used in ICUs and related areas like an Acute Care Unit in order to enable patients who cannot speak to effectively communicate with their care providers and families. Many other categories of patient may be a good fit for this device, since a number of the conditions that cause partial or total loss of speech capability also affect motor abilities, and these patients similarly would benefit from the use of a device that allows users with imperfect motor capabilities to produce speech output.

In various embodiments, patients who may find the systems and methods of the invention of use include that suffer from nasopharyngeal cancer, ALS, and oter diseases that diminish their ability to speak, whether they are in a hospital, an extended care facility or are outpatients.

In various embodiments, the systems and methods of the invention are useful for persons with chronic visual impairments, by providing such as visual output as large print, high contrast, and distinguishable shapes so as to help color-blind individuals In various embodiments, the systems and methods of the invention are useful to persons who have auditory problems, by providing higher volume, and/or the use of a Bluetooth speaker situated proximate to a user's ear to improve volume.

In various embodiments, the systems and methods of the invention are useful to provide cognitive stimulation to patients in a hospital or extended care context.

In various embodiments, the systems and methods of the invention are useful to allow a user to specify category of conversation, such as specific topics of interest for discussion with medical professionals.

In various embodiments, the systems and methods of the invention are useful to allow data logging for analysis of an individual's condition, progress, and historical record.

In various embodiments, the systems and methods of the invention are operable using any mode of operation selected from "tilt and click" (or "tilt and press", "tilt and squeeze"), type, and hold a selection for a minimum dwell time.

In various embodiments, the systems and methods of the invention are capable of providing word completion, for example, in the instance that a patient types the string "ne"

the system may display the words "need", "new", and "never", thereby allowing the person to select an entire word after tying just the first few letters.

In some embodiments, the systems and methods of the invention allow data logging, so that hospital staff can tabulate data from one or more tablets in terms of use statistics, to allow compilation of requests from and interactions with patients and improve staff understanding of patient needs.

In some embodiments, the systems and methods of the invention allow the display of pictures added to selection screens. The use of pictures instead of word can be helpful to low literacy patients, patients with blurry vision, patients with impaired cognition (temporary or permanent), and patients with language barriers. For example, a picture of a water fountain, or a picture of a toilet may be helpful in place of the words "thirsty" and "toilet" to a patent who does not know how to read.

Software Listing

A software listing is being filed herewith as a text (.txt) file, which comprises 37 pages of code, which is incorporated by reference herein in its entirety.

Definitions

Any reference in the claims to an electronic signal or an electromagnetic signal (or their equivalents) is to be understood that in a preferred embodiment the signal is a non-transitory electronic signal or a non-transitory electromagnetic signal. If the signal per se is not claimed, the reference may in some instances be to a description of a propagating or transitory electronic signal or electromagnetic signal.

While the [present embodiments have been described as "cylindrical" or "approximately cylindrical" they should be understood to differ from conventional keyboards that are planar or sometimes curved in an ergonomic fashion put which are intended to rest on a surface and to be manipulated by hand, and they should also be understood to differ from conventional joysticks which are intended to rest on a surface and to be manipulated by hand.

Recording the results from an operation or data acquisition, such as for example, recording results at a particular frequency or wavelength, is understood to mean and is defined herein as writing output data in a non-transitory manner to a storage element, to a machine-readable storage medium, or to a storage device. Non-transitory machine-readable storage media that can be used in the invention include electronic, magnetic and/or optical storage media, such as magnetic floppy disks and hard disks; a DVD drive, a CD drive that in some embodiments can employ DVD disks, any of CD-ROM disks (i.e., read-only optical storage disks), CD-R disks (i.e., write-once, read-many optical storage disks), and CD-RW disks (i.e., rewriteable optical storage disks); and electronic storage media, such as RAM, ROM, EPROM, Compact Flash cards, PCMCIA cards, or alternatively SD or SDIO memory; and the electronic components (e.g., floppy disk drive, DVD drive, CD/CD-R/CD-RW drive, or Compact Flash/PCMCIA/SD adapter) that accommodate and read from and/or write to the storage media. Unless otherwise explicitly recited, any reference herein to "record" or "recording" is understood to refer to a non-transitory record or a non-transitory recording.

As is known to those of skill in the machine-readable storage media arts, new media and formats for data storage are continually being devised, and any convenient, commercially available storage medium and corresponding read/write device that may become available in the future is likely to be appropriate for use, especially if it provides any of a greater storage capacity, a higher access speed, a smaller size, and a lower cost per bit of stored information. Well known older machine-readable media are also available for use under certain conditions, such as punched paper tape or cards, magnetic recording on tape or wire, optical or magnetic reading of printed characters (e.g., OCR and magnetically encoded symbols) and machine-readable symbols such as one and two dimensional bar codes. Recording image data for later use (e.g., writing an image to memory or to digital memory) can be performed to enable the use of the recorded information as output, as data for display to a user, or as data to be made available for later use. Such digital memory elements or chips can be standalone memory devices, or can be incorporated within a device of interest. "Writing output data" or "writing an image to memory" is defined herein as including writing transformed data to registers within a microcomputer.

"Microcomputer" is defined herein as synonymous with microprocessor, microcontroller, and digital signal processor ("DSP"). It is understood that memory used by the microcomputer, including for example instructions for data processing coded as "firmware" can reside in memory physically inside of a microcomputer chip or in memory external to the microcomputer or in a combination of internal and external memory. Similarly, analog signals can be digitized by a standalone analog to digital converter ("ADC") or one or more ADCs or multiplexed ADC channels can reside within a microcomputer package. It is also understood that field programmable array ("FPGA") chips or application specific integrated circuits ("ASIC") chips can perform microcomputer functions, either in hardware logic, software emulation of a microcomputer, or by a combination of the two. Apparatus having any of the inventive features described herein can operate entirely on one microcomputer or can include more than one microcomputer.

General purpose programmable computers useful for controlling instrumentation, recording signals and analyzing signals or data according to the present description can be any of a personal computer (PC), a microprocessor based computer, a portable computer, or other type of processing device. The general purpose programmable computer typically comprises a central processing unit, a storage or memory unit that can record and read information and programs using machine-readable storage media, a communication terminal such as a wired communication device or a wireless communication device, an output device such as a display terminal, and an input device such as a keyboard. The display terminal can be a touch screen display, in which case it can function as both a display device and an input device. Different and/or additional input devices can be present such as a pointing device, such as a mouse or a joystick, and different or additional output devices can be present such as an enunciator, for example a speaker, a second display, or a printer. The computer can run any one of a variety of operating systems, such as for example, any one of several versions of Windows, or of MacOS, or of UNIX, or of Linux. Computational results obtained in the operation of the general purpose computer can be stored for later use, and/or can be displayed to a user. At the very least, each microprocessor-based general purpose computer has registers that store the results of each computational step within the microprocessor, which results are then commonly stored in cache memory for later use, so that the result can be displayed, recorded to a non-volatile memory, or used in further data processing or analysis.

Many functions of electrical and electronic apparatus can be implemented in hardware (for example, hard-wired logic), in software (for example, logic encoded in a program operating on a general purpose processor), and in firmware (for example, logic encoded in a non-volatile memory that is invoked for operation on a processor as required). The present invention contemplates the substitution of one implementation of hardware, firmware and software for another implementation of the equivalent functionality using a different one of hardware, firmware and software. To the extent that an implementation can be represented mathematically by a transfer function, that is, a specified response is generated at an output terminal for a specific excitation applied to an input terminal of a "black box" exhibiting the transfer function, any implementation of the transfer function, including any combination of hardware, firmware and software implementations of portions or segments of the transfer function, is contemplated herein, so long as at least some of the implementation is performed in hardware.

Theoretical Discussion

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

INCORPORATION BY REFERENCE

Any patent, patent application, patent application publication, journal article, book, published paper, or other publicly available material identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. A communication system, comprising:
    a cylindrical hand operated input device comprising:
        five pressure switches, each pressure switch being positioned to be accessible by a fingertip of a user's hand and having an electrical signal output port, wherein said pressure switches are configured to accept input conveyed by mechanical motion of each finger and configured to convert said input conveyed by mechanical motion into an electrical signal, and
        a tilt device configured to provide four tilt directions allowing said input device to operate in a tilt mode, wherein said user is capable of making a selection of an action by a tilt motion to provide an electrical signal output port;
    a general purpose programmable computer that is configured to operate under the control of a set of instructions recorded in a non-volatile manner on a machine readable medium, said general purpose programmable computer comprising five input ports configured to receive said electrical signal from each of said electrical signal output ports of said cylindrical hand operated input device, said general purpose programmable computer being configured to interpret and process said received signal and to generate a response signal at a response signal output port; and
    a display device configured to receive said response signal from said response signal output port and to provide an output signal in at least one of visual and audible form to said user of said communication system.

2. The communication system of claim 1, wherein said cylindrical hand operated input device comprises four keys.

3. The communication system of claim 1, wherein said mechanical motion comprises a press motion.

4. The communication system of claim 1, wherein said general purpose programmable computer is integrated with said cylindrical hand operated input device.

5. The communication system of claim 1, wherein said general purpose programmable computer is mechanically separate from said cylindrical hand operated input device.

6. The communication system of claim 1, wherein any two of said cylindrical hand operated input device, said general purpose programmable computer and said display device are connected by a wired connection.

7. The communication system of claim 1, wherein any two of said cylindrical hand operated input device, said general purpose programmable computer and said display device are connected by a wireless connection.

8. The communication system of claim 1, wherein said cylindrical hand operated input device comprises a structure that holds said cylindrical hand operated input device in proximity to said hand of said user.

9. The communication system of claim 1, wherein said communication system is configured to display prompts to said user in a first language, and to display user responses in a second language.

10. A method of communication with a patient unable to speak, comprising providing said patient a communication system of claim 1, said patient to communicate by mechanical motion of patient's fingers thereby generating output signals to a general-purpose programmable computer and at least one of visual and audible form on a display device.

* * * * *